(12) United States Patent
Wang et al.

(10) Patent No.: US 11,530,424 B1
(45) Date of Patent: Dec. 20, 2022

(54) EFFICIENT CRISPR/HDR-MEDIATED KNOCK-IN SYSTEM AND METHOD OF USE

(71) Applicants: Jia-Wang Wang, Tampa, FL (US); Richard F. Lockey, Tampa, FL (US)

(72) Inventors: Jia-Wang Wang, Tampa, FL (US); Richard F. Lockey, Tampa, FL (US)

(73) Assignees: University of South Florida, Tampa, FL (US); United States Department of Veterans Affairs, Washington, DC (US)

( * ) Notice: Subject to any disclaimer, the term of this patent is extended or adjusted under 35 U.S.C. 154(b) by 540 days.

(21) Appl. No.: 16/587,405

(22) Filed: Sep. 30, 2019

Related U.S. Application Data

(63) Continuation of application No. 15/269,195, filed on Sep. 19, 2016, now abandoned.

(60) Provisional application No. 62/220,674, filed on Sep. 18, 2015.

(51) Int. Cl.
*C12N 15/90* (2006.01)
*C12N 15/85* (2006.01)

(52) U.S. Cl.
CPC .......... *C12N 15/907* (2013.01); *C12N 15/85* (2013.01)

(58) Field of Classification Search
None
See application file for complete search history.

(56) References Cited

U.S. PATENT DOCUMENTS

2016/0208243 A1* 7/2016 Zhang .................... C12N 15/85

OTHER PUBLICATIONS

Zhang L, Jia R, Palange NJ, Satheka AC, Togo J, An Y, et al. (2015) Large Genomic Fragment Deletions and Insertions in Mouse Using CRISPR/Cas9. PLoS ONE 10(3): e0120396. doi:10.1371/ (Year: 2015).*
Yang et al (2014) (Generating genetically modified mice using CRISPR/Cas-mediated genome engineering, nature protocols, vol. 8, Jul. 24, 2014). (Year: 2014).*
Chu, et al., Increasing the efficiency of homology-directed repair for CRISPR-Cas9-induced precise gene editing in mammalian cells. Nat. Biotechnol. May 2015;33(5):543-8.
Doudna & Charpentier, Genome editing. The new frontier of genome engineering with CRISPR-Cas9. Science. Nov. 28, 2014;346(6213):1258096.
Jinek, et al., A programmable dual-RNA-guided DNA endonuclease in adaptive bacterial immunity. Science. Aug. 17, 2012;337(6096):816-21.
Li, et al., Optimization of genome engineering approaches with the CRISPR/Cas9 system. PLoS One. Aug. 28, 2014;9(8):e105779.
Li, et al., A versatile reporter system for CRISPR-mediated chromosomal rearrangements. Genome Biol. May 28, 2015;16:111.
Maruyama, et al., Increasing the efficiency of precise genome editing with CRISPR-Cas9 by inhibition of nonhomologous end joining. Nat. Biotechnol. May 2015;33(5):538-42.
Orlando, et al., Zinc-finger nuclease-driven targeted integration into Mamm. Genomes using donors with limited chromosomal homology. Nucleic Acids Res. Aug. 2010;38(15):e152.
Shulman, et al., Homologous recombination in hybridoma cells: dependence on time and fragment length. Mol Cell Biol. Sep. 1990;10(9):4466-72.
Singh, et al., A mouse geneticist's practical guide to CRISPR applications. Genetics. Jan. 2015;199(1):1-15.
Smith, Theoretical mechanisms in targeted and random integration of transgene DNA. Reprod Nutr Dev. Nov.-Dec. 2001;41(6):465-85.
Song, et al., Modeling disease in human ESCs using an efficient BAC-based homologous recombination system. Cell Stem Cell. Jan. 8, 2010;6(1):80-9.
Tang, et al., Interaction of hsa-miR-381 and glioma suppressor LRRC4 is involved in glioma growth. Brain Res. May 16, 2011;1390:21-32).
Thieme, et al., Quick and clean cloning: a ligation-independent cloning strategy for selective cloning of specific PCR products from non-specific mixes. PLoS One 2011;6(6):e20556.
Thomas & Capecchi, Site-directed mutagenesis by gene targeting in mouse embryo-derived stem cells. Cell. Nov. 1987;51(3):503-12.
Wang, et al., CRISPR/Cas9 nuclease cleavage combined with Gibson assembly for seamless cloning. Biotechniques. Apr. 1, 2015;58(4):161-70.
Wang, et al., Deregulated expression of LRBA facilitates cancer cell growth. Oncogene. May 20, 2004;23(23):4089-97.
Wang, et al., One-Step Generation of Mice Carrying Mutations in Multiple Genes by CRISPR/Cas-Mediated Genome Engineering. Cell. May 9, 2013;153(4):910-8.

(Continued)

*Primary Examiner* — Laura B Goddard
*Assistant Examiner* — Sarah A Alsomairy
(74) *Attorney, Agent, or Firm* — Michele L. Lawson; Smith & Hopen, P.A.

(57) ABSTRACT

The clustered regularly interspaced short palindromic repeat (CRISPR) gene editing technique, based on the non-homologous end-joining (NHEJ) repair pathway, can efficiently generate gene knockouts of variably sizes. More precise genome editing, either the insertion or deletion of a desired fragment, can be done by combining the homology-directed-repair (HDR) pathway with CRISPR cleavage. HDR-mediated gene knock-in experiments are inefficient, with no reports of successful gene knock-in with DNA fragments larger than 4 kb. Targeted insertion of large DNA fragments (7.4 and 5.8 kb) into the genomes of mouse embryonic stem cells and zygotes, respectively, using the CRISPR/HDR technique without NHEJ inhibitors was performed and indicate that CRISPR/HDR without NHEJ inhibitors can result in highly efficient gene knock-in, equivalent to CRISPR/HDR with NHEJ inhibitors. Although NHEJ is the dominant repair pathway associated with CRISPR-mediated double-strand breaks (DSBs), and biallelic gene knock-ins are common, NHEJ and biallelic gene knock-ins were not detected.

8 Claims, 9 Drawing Sheets

Specification includes a Sequence Listing.

(56) References Cited

OTHER PUBLICATIONS

Warming, et al., Simple and highly efficient BAC recombineering using galK selection. Nucleic Acids Res. Feb. 24, 2005;33(4):e36.
Yang, et al., One-step generation of mice carrying reporter and conditional alleles by CRISPR/Cas-mediated genome engineering. Cell. Sep. 12, 2013;154(6):1370-9.
Non-Final Office Action dated Nov. 15, 2017 for corresponding U.S. Appl. No. 15/269,195.
Final Office Action dated Apr. 20, 2018 for corresponding U.S. Appl. No. 15/269,195.
Advisory Action dated Aug. 7, 2018 for corresponding U.S. Appl. No. 15/269,195.
Non-Final Office Action dated Feb. 7, 2019 for corresponding U.S. Appl. No. 15/269,195.

* cited by examiner

EFFICIENT CRISPR/HDR-MEDIATED KNOCK-IN SYSTEM AND METHOD OF USE

CROSS REFERENCE TO RELATED APPLICATIONS

This application is a continuation of and claims priority to currently pending U.S. Nonprovisional application Ser. No. 15/269,195, entitled "Efficient CRISPR/HDR-Mediated Knock-In System and Method of Use", filed Sep. 19, 2016, which claims priority to U.S. Provisional Patent Application Ser. No. 62/220,674, entitled "Efficient CRISPR Knockin", filed Sep. 18, 2015, the contents of each of which are hereby incorporated by reference into this disclosure.

FIELD OF INVENTION

This invention relates to gene therapy. Specifically, the invention relates to using enzymatic excision of genetic material and replacement using homology-directed-repair.

BACKGROUND OF THE INVENTION

Genome editing is a powerful tool to study gene function. The clustered regularly interspaced short palindromic repeat (CRISPR) system is an adaptive immune system found in bacteria. It can destroy naturally occurring and engineered phages and plasmids (Wiedenheft, et al., RNA-guided genetic silencing systems in bacteria and archaea. Nature. 2012 Feb. 15; 482(7385):331-8). A CRISPR genome editing tool was developed based on this system and has been used to edit the genomes of many species (Brown, et al., Whole-rat conditional gene knockout via genome editing. Nat. Methods 2013 July; 10(7):638-40; Cong, et al., Multiplex genome engineering using CRISPR/Cas systems. Science. 2013 Feb. 15; 339(6121):819-23; Wang, et al., One-Step Generation of Mice Carrying Mutations in Multiple Genes by CRISPR/Cas-Mediated Genome Engineering. Cell. 2013 May 9; 153(4):910-8). CRISPR cleavage causes DNA double-strand breaks (DSBs), which are usually repaired by the nonhomologous end-joining (NHEJ) repair pathway (Lieber, The mechanism of doublestrand DNA break repair by the nonhomologous DNA end-joining pathway. Annu. Rev. Biochem. 2010; 79:181-211; Frit, et al., Alternative end-joining pathway(s): bricolage at DNA breaks. DNA Repair (Amst). 2014 May; 17:81-97). NHEJ is an error-prone process that often causes insertion/deletion (indel) mutations, a portion of which result in frameshift mutations. In one study, a 51%-79% CRISPR-targeting efficiency was obtained for different genes in human embryonic stem (ES) cells. Similarly, CRISPR-induced mutation rates of up to 78% were obtained in mice (Wang, et al., One-Step Generation of Mice Carrying Mutations in Multiple Genes by CRISPR/Cas-Mediated Genome Engineering. Cell. 2013 May 9; 153(4):910-8; Yang, et al., One-step generation of mice carrying reporter and conditional alleles by CRISPR/Cas-mediated genome engineering. Cell. 2013 Sep. 12; 154(6):1370-9; Zhou, et al., Dual sgRNAs facilitate CRISPR/Cas9-mediated mouse genome targeting. FEBS J. 2014 April; 281(7):1717-25; Fujii, et al., Efficient generation of large-scale genome-modified mice using gRNA and CAS9 endonuclease. Nucleic Acids Res. 2013 November; 41(20):e187).

For precise genome editing by inserting or deleting a designed fragment, gene targeting based on homologous recombination (HR) is often the preferred methodology. However, the efficiency of traditional gene targeting is generally low, ranging from undetectable to 0.1% (Bollag, et al., Homologous recombination in mammalian cells. Annu. Rev. Genet. 1989; 23:199-225). The DSBs induced by CRISPR can also be repaired through the homology-directed-repair (HDR) pathway. Here, a DNA fragment flanked by two sequences that are homologous to the sequences flanking the cleaved site can be inserted into the cleaved site by HR with efficiencies 5000 times higher than traditional HR (Donoho, et al., Analysis of gene targeting and intrachromosomal homologous recombination stimulated by genomic double-strand breaks in mouse embryonic stem cells. Mol Cell Biol. 1998 July; 18(7):4070-8).

Gene knock-in techniques mediated by the CRISPR/HDR pathway have been less well studied, but CRISPR/HDR targeting efficiencies have been reported to be only in the range of 0.5-20%, much lower than the efficiency of CRISPR mediated by NHEJ (Wang, et al., One-Step Generation of Mice Carrying Mutations in Multiple Genes by CRISPR/Cas-Mediated Genome Engineering. Cell. 2013 May 9; 153(4):910-8; Yang, et al., One-step generation of mice carrying reporter and conditional alleles by CRISPR/Cas-mediated genome engineering. Cell. 2013 Sep. 12; 154(6):1370-9). Since HDR and NHEJ compete with each other for the same DSB site, the efficiency of HDR can be significantly increased by inhibiting NHEJ (Maruyama, et al., Increasing the efficiency of precise genome editing with CRISPR-Cas9 by inhibition of nonhomologous end joining. Nat. Biotechnol. 2015 May; 33(5):538-42; Chu, et al., Increasing the efficiency of homology-directed repair for CRISPR-Cas9-induced precise gene editing in mammalian cells. Nat. Biotechnol. 2015 May; 33(5):543-8). However, because NHEJ is essential for DNA repair and embryonic viability, its deficiency may cause deleterious effects, such as mutagenesis and toxicity. Furthermore, it is unknown whether or not inhibiting NHEJ is effective for knocking in a DNA fragment at any locus, especially large fragments (>4 kb) containing multiple genes or a single large gene. So far, only small inserts and a few loci have been tested with this method (Maruyama, et al., Increasing the efficiency of precise genome editing with CRISPR-Cas9 by inhibition of nonhomologous end joining. Nat. Biotechnol. 2015 May; 33(5):538-42; Chu, et al., Increasing the efficiency of homology-directed repair for CRISPR-Cas9-induced precise gene editing in mammalian cells. Nat. Biotechnol. 2015 May; 33(5):543-8). More importantly, the targeting efficiency of CRISPR in vivo is only ~3% (Xue, et al., CRISPR-mediated direct mutation of cancer genes in the mouse liver. Nature. 2014 Oct. 16; 514(7522):380-4). Therefore, additional investigation is required to enhance gene knock-in efficiencies for larger DNA fragments.

SUMMARY OF INVENTION

Here, large DNA fragments, 7.4 and 5.8 kb, were knocked in to the genomes of mouse ES cells and zygotes, respectively, using the CRISPR/HDR technique without any NHEJ inhibitors, at high efficiencies equivalent to that of CRISPR/NHEJ knockout in human ES cells (Ding, et al., Enhanced efficiency of human pluripotent stem cell genome editing through replacing TALENs with CRISPRs. Cell Stem Cell. 2013 Apr. 4; 12(4):393-4) and to that of CRISPR/HDR using NHEJ inhibitors (Maruyama, et al., Increasing the efficiency of precise genome editing with CRISPR-Cas9 by inhibition of nonhomologous end joining. Nat. Biotechnol. 2015 May; 33(5):538-42; Chu, et al., Increasing the efficiency of homology-directed repair for CRISPR-Cas9-induced precise gene editing in mammalian cells. Nat. Biotechnol. 2015 May;

33(5):543-8). Furthermore, a high survival rate of zygotes was obtained by injecting only one fourth of the regular concentrations of CRISPR reagents. This study also demonstrates that NHEJ inhibitors and homologous sequences longer than 2.2 kb are not prerequisites for knocking in a large (7.4 kb) fragment into the genomic locus of the gene under study at high efficiency.

The method is used to edit a host genome by knocking in a large DNA fragment into a target gene sequence of a host in the absence of non-homologous end joining (NHEJ) inhibitor. At least one clustered regularly interspaced short palindromic repeat (CRISPR) system is inserted into a cell to edit the host genome. The CRISPR system is comprised of a single guide RNA and a donor DNA, which may be found in different vectors. Additionally, a nucleotide encoding a CRISPR endonuclease, which is disposed in the same vector as the single guide RNA, or as an independent nucleotide molecule, i.e. not associated with the single guide RNA or donor DNA. Once the at least one CRISPR system is inserted into the cell, the cell is allowed to undergo homology-directed-repair. The CRISPR endonuclease excises nucleotides of the target sequence and homology-directed-repair used to replace the target sequence.

The single guide RNA (sgRNA) comprises a crRNA sequence, complementary to the target sequence, and a transactivating crRNA (tracrRNA) hybridized to the crRNA sequence and interacting with the CRISPR endonuclease. The DNA sequences that encode the sgRNA and CRISPR endonuclease are usually located in the same DNA vector. Alternatively, an sgRNA and an RNA sequence encoding the CRISPR endonuclease are provided as two separate RNA molecules. The CRISPR endonuclease is optionally Cas9 (SEQ ID No. 26) or Cpf1 (SEQ ID No. 27). Where Cpf1 is used, the tracrRNA is not required. A donor DNA sequence, comprised of the repair sequence DNA fragment flanked by two arms which are homologous to the flanking sequences of the target sequence in the target gene of the host, is provided. The repair sequence is a gene sequence for insertion into the genome of the cell, which can be a non-mutated replacement gene or other genetic material. The repair sequence DNA fragment is at least 1 kb in length. Nonlimiting examples include 1 kb, 1.1 kb, 1.2 kb, 1.3 kb, 1.4 kb, 1.5 kb, 1.6 kb, 1.7 kb, 1.8 kb, 1.9 kb, 2.0 kb, 2.1 kb, 2.1 kb, 2.2 kb, 2.3 kb, 2.4 kb, 2.5 kb, 2.6 kb, 2.7 kb, 2.8 kb, 2.9 kb, 3.0 kb, 3. kb, 3.2 kb, 3.3 kb, 3.4 kb, 3.5 kb, 3.6 kb, 3.7 kb, 3.8 kb, 3.9 kb, 4.0 kb, 4.1 kb, 4.2 kb, 4.3 kb, 4.4 kb, 4.5 kb, 4.6 kb, 4.7 kb, 4.8 kb, 4.9 kb, 5.0 kb, 5.1 kb, 5.2 kb, 5.3 kb, 5.4 kb, 5.5 kb, 5.6 kb, 5.7 kb, 5.8 kb, 5.9 kb, 6.0 kb, 6.1 kb, 6.2 kb, 6.3 kb, 0.4 kb, 6.5 kb, 6.6 kb, 6.47 kb, 6.8 kb, 6.9 kb, 7.0 kb, 7.1 kb, 7.2 kb, 7.3 kb, 7.4 kb, 7.5 kb, 0.6 kb, 7.7 kb, 7.8 kb, 7.9 kb, 8.0 kb, 8.1 kb, 8.2 kb, 8.3 kb, 8.4 kb, 8.5 kb, 8.6 kb, 8.7 kb, 8.8 kb, 8.9 kb, 9.0 kb, 9.2 kb, 9.4 kb, 9.5 kb, 9.6 kb, 9.8 kb, or 10 kb.

In specific variations, the vector may be linearized. The CRISPR system may inserted into the vector using Gibson Assembly or quick and clean cloning. Alternatively, the CRISPR system may be inserted into a cell by electroporation or microinjection. Where microinjection is used, the single guide RNA, the CRISPR endonuclease, and the donor DNA are mixed into a microinjection buffer to form a microinjection solution, and the microinjection solution injected into the cell. In specific variations, the microinjection components are mixed in a ratio of single guide RNA to CRISPR endonuclease nucleotide to donor DNA of 1:2:4. The CRISPR method is optionally performed on a zygote or stem cell. The method is optionally performed without a non-homologous end joining inhibitor.

The methods described above can be used to treat or prevent a genetic disorder by inserting the CRISPR system into a cell, which is allowed to undergo homology-directed-repair. The genetic disorder is cancer, an autoimmune disorder, or Lrba-associated disease. The method can target tumor suppressor proteins, such as p53, retinoblastoma protein, PTEN, pVHL, CD95, ST14, YPEL3, APC. The method can alteratively target oncogenes, such as Ras, myc, Raf, Src proteins, BTK proteins, Sis protein, tyrosine kinase receptors, such as EGFR, PDGFR, and VEGFR, and cell cycle checkpoint proteins, such as p16, cdk4, cdk6, cyclin D1, cyclin D2, cyclin D3. The targeted gene is aberrant, i.e. mutated or under improper transcriptional control. The methods herein are designed to target these cellular systems and correct the mutation through replacement, or control transcription through reduced activation (less efficient transcription, etc.). Immune diseases can unclude defects in antibody encoding or transcription, TAP mutations affecting MHC class I proteins, mutations in MHC class II, mutated CD40 ligand, mutated Blk tyrosine kinase, mutations in the gamma immunoglobin chain, mutations in SH2D1A, and Lrba-associated diseases include cvid8, immunodeficiency, t-lymphocyte deficiency, and autoimmune diseases.

BRIEF DESCRIPTION OF THE DRAWINGS

For a fuller understanding of the invention, reference should be made to the following detailed description, taken in connection with the accompanying drawings, in which.

Figure 5:
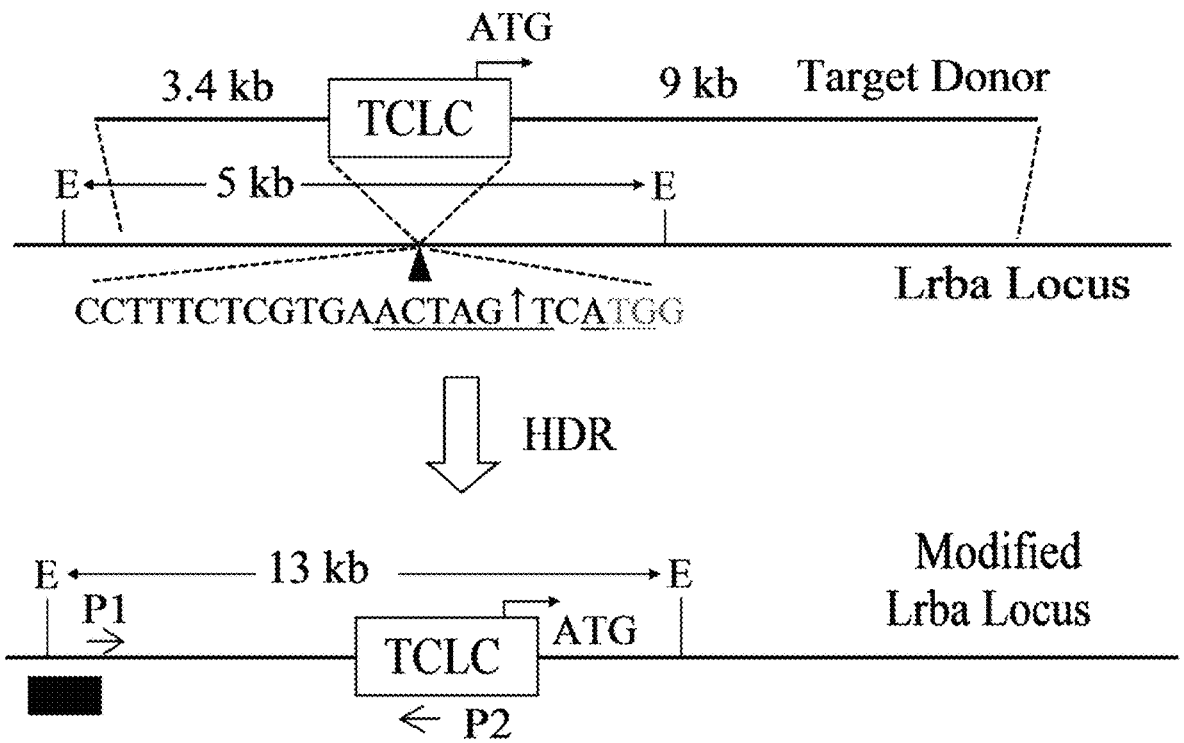

FIG. 5 Strategy to knock a transcription control and labeling cassette (TCLC) (SEQ ID NO:28) into the Lrba locus in mouse ES cells through CRISPR/HDR technique. The sgRNA sequence is in black, and the protospacer-adjacent motif (PAM) sequence (NGG) is in gray. The underlined sequences are SpeI cleavage site and the translation start codon of Lrba. The cleavage site of Cas9 nuclease is indicated by an arrow. HDR by the left and right arms (black bars) of the target donor will then insert the TCLC into the Lrba locus between the promoter and the Lrba translation start codon (ATG). The box under the gene indicates the Southern blotting probe.

Figure 6:
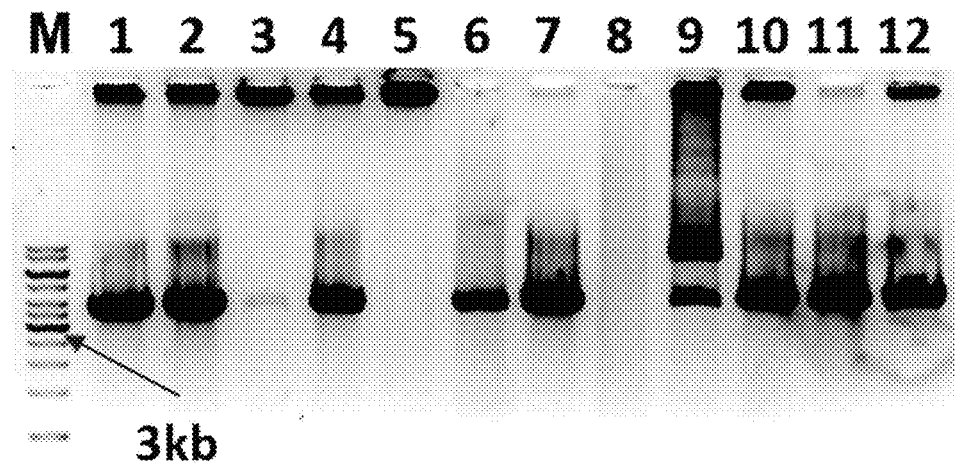

FIG. 6 is a blot showing the PCR screening for Lrba knockin-positive ES clones targeted by CRISPR/HDR. The predicted size of the PCR product is 3.5 kb.

Figure 7:
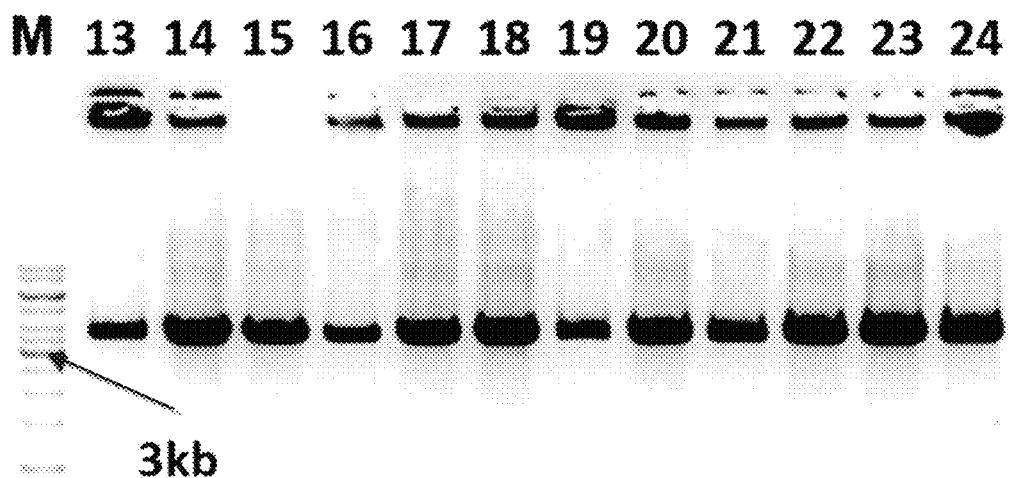

FIG. 7 is a blot showing the PCR screening for Lrba knockin-positive ES clones targeted by CRISPR/HDR. The predicted size of the PCR product is 3.5 kb. Clone #13, 16 and 19 were counted as negatives because the intensity of these bands was much weaker than that of positive ones.

Figure 8:
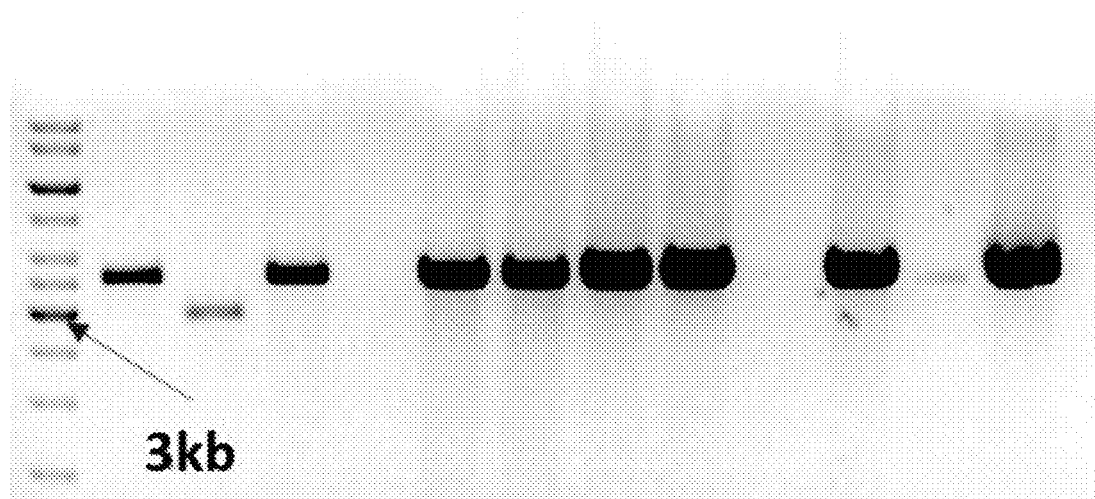

FIG. 8 is a blot showing the PCR screening for Lrba knockin-positive ES clones targeted by CRISPR/HDR. The predicted size of the PCR product is 3.5 kb.

Figure 9:
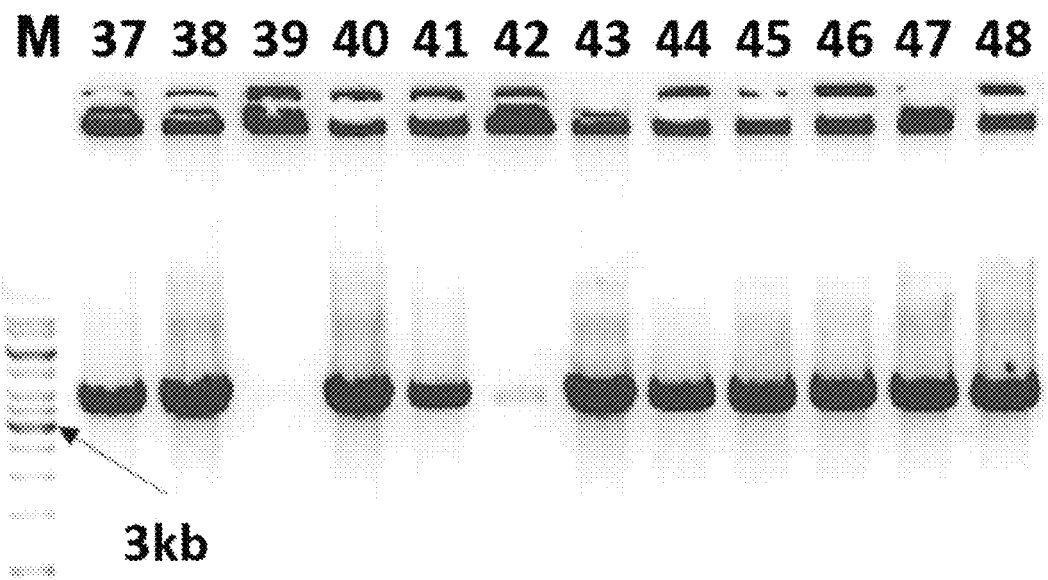

FIG. 9 is a blot showing the PCR screening for Lrba knockin-positive ES clones targeted by CRISPR/HDR. The predicted size of the PCR product is 3.5 kb.

Figure 10:
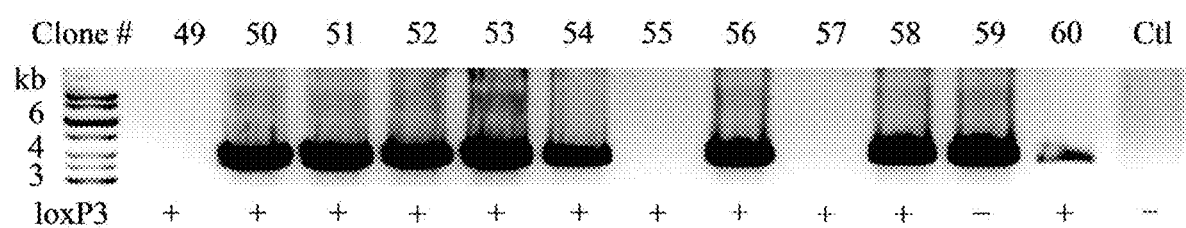

FIG. 10 is a blot showing the PCR screening for Lrba knockin-positive ES clones targeted by CRISPR/HDR. The predicted size of the PCR product is 3.5 kb. Ctl, control, PCR template was from untargeted ES cells. loxP3, the third loxP site.

Figure 11:
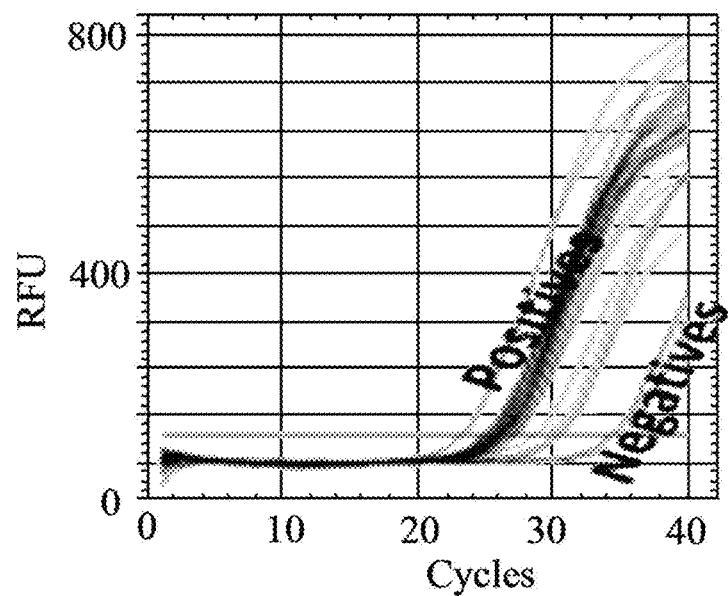

FIG. 11 is a graphs showing characterization of mouse ES cell targeted by CRISPR/HDR. The presence of the third loxP site in ES clones was detected by real time PCR using the loxP sequence as a Taqman probe. RFU, Relative fluorescence units. Positives, with the presence of the third loxP sites and negatives, without the presence of the third loxP sites.

Figure 12:
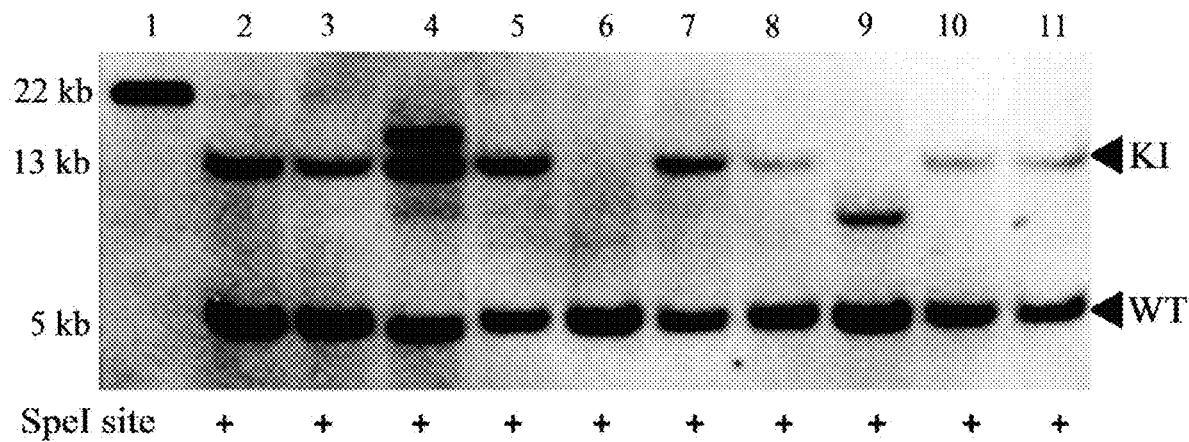

FIG. 12 is a blot showing Southern blotting results of mouse ES cell targeted by CRISPR/HDR. EcoRV-digested genomic DNA was hybridized with a 5' external probe with expected fragment sizes of 5 kb (WT) and 13 kb (knockin, KI). 1. Linearized donor vector (22 kb, 100 pg) control. Others: G418-positive clones. #4 and #9 were incorrectly targeted, and #6 WT. The other clones (#2, 3, 5, 7, 8, 10, and 11) were correctly targeted heterozygotes.

Figure 13:
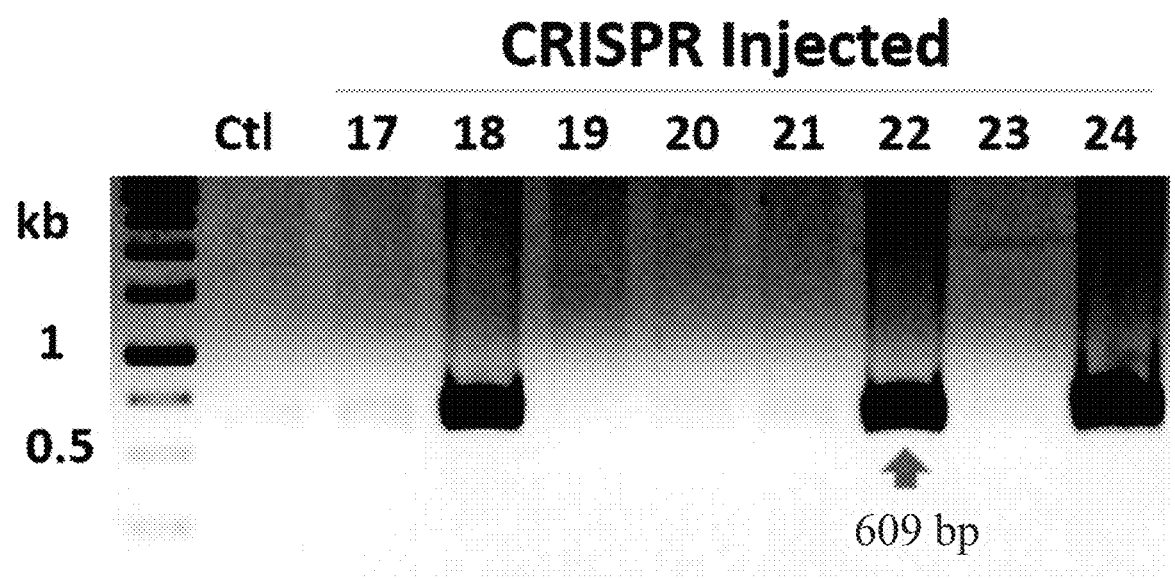

FIG. 13 is a blot showing Southern blotting results of mouse blastocysts targeted by CRISPR/HDR.Nested PCR detection of correctly targeted blastocysts derived from zygotes injected with CRISPR reagents. One quarter of DNA from a blastocyst was used for the first PCR as in A. Ctl, control, PCR template was from an uninjected zygotes.

Figure 14:
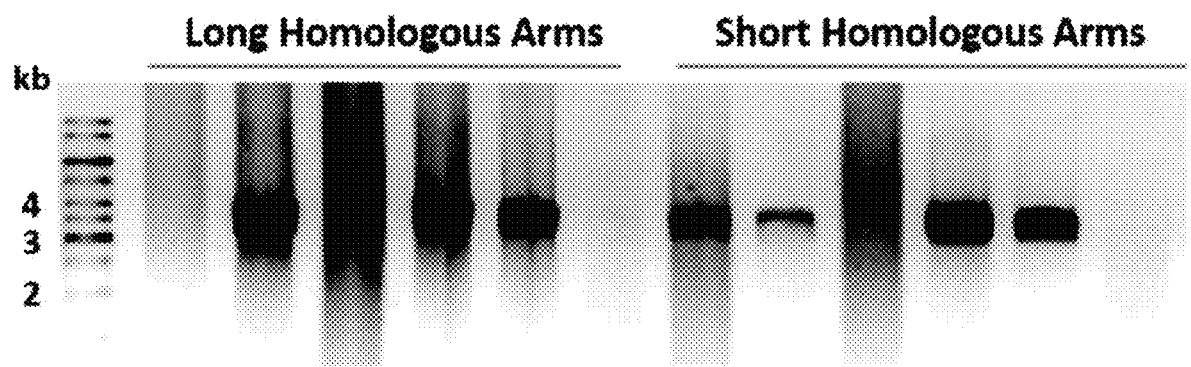

FIG. 14 is a blot showing CRISPR/HDR and CRISPR/NHEJ pathways. Parallel comparison of targeting efficiency of two targeting vectors with different lengths of homologous arms flanking the same insert, as seen in Table 9. 30 G418-positive ES clones were picked up and subjected to PCR screening of Lrba knockin-positive ES clones. The predicted size of the PCR product is 3.5 kb. Representative results are shown.

Figure 15:
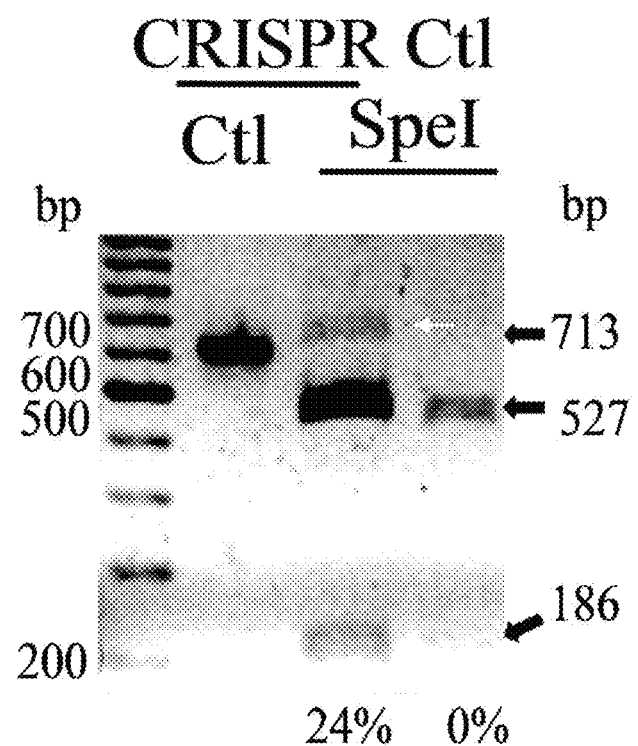

FIG. 15 is a blot showing CRISPR/HDR and CRISPR/NHEJ pathways. SpeI digestion of PCR product using genomic DNA from ES cells transfected with Lrba sgRNA/Cas9 vector. SpeI digestion of the PCR product, 713 bp, produces 527 bp and 186 bp fragments in wt but cannot cut the CRISPR mutated allele (arrow) as the SpeI site was destroyed by CRISPR. The percentage at the bottom are the estimated targeting efficiencies. Ctl, no SpeI, undigested PCR product. Representative results are shown.

Figure 16:
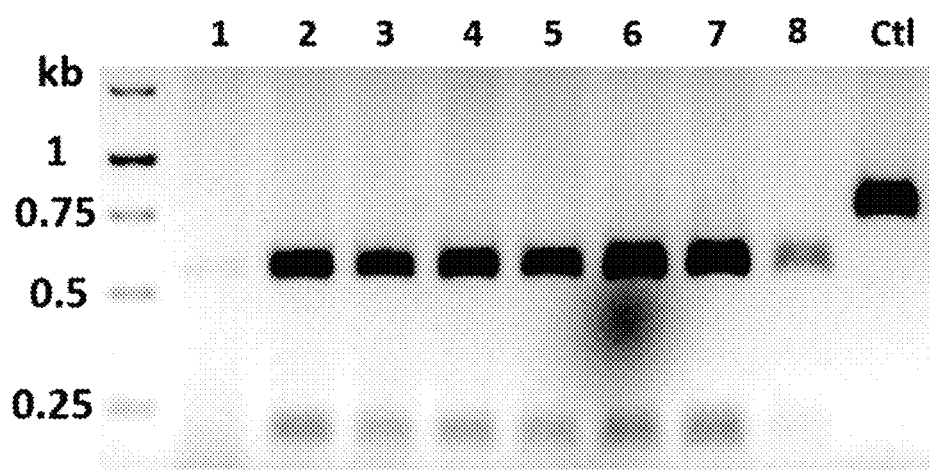

FIG. 16 is a blot showing CRISPR/HDR and CRISPR/NHEJ pathways. Detection of CRISPR/NHEJ-mediated mutations in ES clones by SpeI digestion. PCR products were obtained from 56 out of 60 ES clones with either targeted or random integration and subjected to SpeI digestion. Ctl, no SpeI, undigested PCR product. Representative results are shown.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

As used herein, "treat", "treatment", "treating", and the like refer to acting upon a condition, such as a neurodegenerative disease, with an agent depending on the desired effect, to affect the condition by improving or altering it. The improvement or alteration may include an improvement in symptoms or an alteration in the physiologic pathways associated with the condition. "Treatment," as used herein, covers one or more treatments of a condition in a host (e.g., a mammal, typically a human or non-human animal of veterinary interest), and includes: (a) reducing the risk of occurrence of the condition in a subject determined to be predisposed to the condition but not yet diagnosed, (b) impeding the development of the condition, and/or (c) relieving the condition, e.g., causing regression of the condition and/or relieving one or more condition symptoms (e.g., reduce inflammation).

As used herein, the terms "prophylactically treat" or "prophylactically treating" refers completely or partially preventing (e.g., about 50% or more, about 60% or more, about 70% or more, about 80% or more, about 90% or more, about 95% or more, or about 99% or more) a condition or symptom thereof and/or may be therapeutic in terms of a partial or complete cure or alleviation for a condition and/or adverse effect attributable to the condition.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one or more such excipients, diluents, carriers, and adjuvants.

The term "therapeutically effective amount" as used herein describes concentrations or amounts of components such as antibodies or other agents which are effective for producing an intended result, including preventing autoimmune disease or immunotolerance, or treating an autoimmune disease, such as rheumatoid arthritis and asthma, or immunotolerance, such as cancer. Compositions according to the present invention may be used to effect a favorable change on immune cells, whether that change is an improvement, such as stopping or reversing the immune disease, or relieving to some extent one or more of the symptoms of the condition being treated, and/or that amount that will prevent, to some extent, one or more of the symptoms of the condition that the host being treated has or is at risk of developing, or a complete cure of the disease or condition treated.

The term "administration" refers to introducing an agent of the present disclosure into a patient. One preferred route of administration of the agent is oral administration. Another preferred route is intravenous administration. However, any route of administration, such as subcutaneous, peritoneal, intraarterial, introduction into the cerebrospinal fluid, or instillation into body compartments can be used.

As used herein, the term "subject," "patient," or "organism" includes humans and mammals (e.g., mice, rats, pigs, cats, dogs, and horses). Typical patients to which an agent(s) of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like.

Example 1

Single guide RNA (sgRNA) vector was prepared using the methods of Wang, et al. (Wang, et al., CRISPR/Cas9 nuclease cleavage combined with Gibson assembly for seamless cloning. Biotechniques. 2015 Apr. 1; 58(4):161-70). Two oligonucleotides (mLAsgF and mLAsgR) were synthesized and annealed to form a double-stranded fragment with the desired overhangs, shown in Table 1, for cloning into the pX330 vector (Addgene plasmid 42230; Addgene, Cambridge, Mass.) (Cong, et al., Multiplex genome engineering using CRISPR/Cas systems. Science. 2013 Feb. 15; 339(6121):819-23). The forward primer mLAsgF, contained 3 parts: a Lrba promoter sequence, the 19-bp guide sequence for the Lrab promoter of vector A1, and the first 20 bases of the tracrRNA sequence from the pX330 vector. The template for the sgRNA (LAgRNA) targeting the LA sequence was PCR amplified from pX330-LAsg using the forward primer mLAsgF containing the T7 promoter sequence and the guide sequence for LA. The 2 oligonucleotides were diluted and mixed together at a final concentration of 10 µM and denatured at 95° C. for 5 min in a PCR machine. The machine was then turned off, and the tube was cooled to room temperature over 30 min. The LA guide sequence double-stranded fragment was cloned into the pX330 vector (Cong, et al., Multiplex genome engineering using CRISPR/Cas systems. Science. 2013 Feb. 15; 339(6121):819-23; Cost, Enzymatic ligation assisted by nucleases: simultaneous ligation and digestion promote the ordered assembly of DNA. Nat Protoc. 2007; 2(9):2198-202).

A PCR reaction mixture contained 2 µl 10× Pfx50 PCR mix, 2.4 µl 2.5 mM dNTP mix, 1.2 µl 10 M forward and reverse primer mix, 0.4 µl plasmid template (2.2 ng/µl), and 0.4 µl Pfx50 DNA polymerase (5 U/µl) (Life Technologies, Grand Island, N.Y.). Sterile distilled water was added to bring the total reaction volume to 20 µl. The PCR cycling parameters were: 94° C. for 2 min, 5 cycles of 94° C. for 15 s and 68° C. for 20 s, 5 cycles of 94° C. for 15 s and 66° C. for 10 s, 68° C. for 20 s, and 25 cycles of 94° C. for 15 s, 63° C. for 10 s and 68° C. for 20 s, and 1 cycle of 68° C. for 10 min. PCR products were extracted with phenol/chloroform and then purified using an S-300 microSpin column (GE Healthcare Bio-Sciences, Pittsburgh, Pa.) following the manufacturer's instructions.

TABLE 1

Oligonucleotides used in generation of LA guide sequence, depicted in bold. Lower case sequence depicts overhangs complementary to overhangs of pX330 cloning vector after BbsI digestion.

| primer | sequence |
|---|---|
| mLAsgF | SEQ ID No. 1 caccGCCTTTCTCGTGAACTAGTCA |
| mLAsgR | SEQ ID No. 2 aaacTGACTAGTTCACGAGAAAGGC |
| mLAgRNA | SEQ ID No. 3 CCTTTCTCGTGAACTAGTCA |
| sgLAF | SEQ ID No. 4 <u>TGTAATACGACTCACTATAGGCC</u> TTTCTCGTGAAC TAGTCA |
| sgRNAR | SEQ ID No. 5 AAAAGCACCGACTCGGTGCC |
| T3gRNAF | SEQ ID No. 6 <u>TGTAATACGACTCACTATAGG</u>CTAAATTAACCCTCA CTAAGTTTTAGAGCTAGAAATAGC |

The resulting product was inserted into linearized pX330 cloning vector. The pX330 vector was cleaved by digesting 1 µg pX330 with 10 U BbsI (Thermo Scientific, Waltham, Mass.), 2 µL 10× Buffer G in the presence of 400 U T4 ligase, 1 µL annealed oligonucleotide (10 µM stock), and 1 mM ATP at 37° C. overnight. Next, 2 µL of the ligation reaction was used to transform competent cells.

The template for the sgRNA (T3gRNA) targeting the T3 promoter sequence in the cloning vector A1 (pLACAGRFPTetOn; 21683 bp) was PCR amplified from pX330 using the forward primer T3gRNAF, which contained 3 parts: a T7 promoter sequence, the 19-bp guide sequence for the T3 promoter of vector A1 (position 12651-12669), and the first 20 bases of the tracrRNA sequence from the pX330 vector (16) (Addgene plasmid 42230) (Table 1). The template for the sgRNA (LAgRNA) targeting the LA sequence was PCR amplified from pX330-LAsg using the forward primer sgLAF containing the T7 promoter sequence and the guide sequence for LA. The same reverse primer (sgRNAR) binding to the sequence (position 347-328) in pX330 was used in both cases. The PCR reaction mixture contained 2 µl 10× Pfx50 PCR mix, 2.4 µl 2.5 mM dNTP mix, 1.2 µl 10 µM forward and reverse primer mix, 0.4 µl plasmid template (2.2 ng/µl), and 0.4 µl Pfx50 DNA polymerase (5 U/µl) (Life Technologies, Grand Island, N.Y.). Sterile distilled water was added to bring the total reaction volume to 20 µl. The PCR cycling parameters were: 94° C. for 2 min, 5 cycles of 94° C. for 15 s and 68° C. for 20 s, 5 cycles of 94° C. for 15 s and 66° C. for 10 s, 68° C. for 20 s, and 25 cycles of 94° C. for 15 s, 63° C. for 10 s and 68° C. for 20 s, and 1 cycle of 68° C. for 10 min. PCR products were extracted with phenol/chloroform and then purified using an S-300 microSpin column (GE Healthcare Bio-Sciences, Pittsburgh, Pa.) following the manufacturer's instructions.

The digestion was carried out in a 30 µl reaction mixture composed of 3 µl 10× Cas9 nuclease reaction buffer, 126 ng (300 nM) sgRNA, and 1 µl 1 µM Cas9 nuclease (NEB). Sterile distilled water was added to bring the total reaction volume to 30 µl. The final concentration of Cas9 nuclease was 30 nM. There is no unit definition for this enzyme from the manufacturer (NEB). The mixture was pre-incubated for 10 min at 37° C. and then 30 nM plasmid DNA was added, and the mixture was incubated for 1 h (as recommended by the manufacturer), overnight, or 72 h, following the manufacturer's protocol. The vector A1 that had been digested overnight was used for Gibson cloning. The overnight Cas9 digested vector was purified.

The PCR-amplified products, Cas9 mRNA and the Cas9/sgRNA digested vector A1 were phenol/chloroform extracted and then purified by an S-300 microspin column as described above. The purified vector (63 ng) and insert (47 ng) mixture (10 µl) was mixed with 10 µl Gibson Assembly Master Mix and incubated at 37° C. for 1 h.

To test the efficiency, the quick and clean cloning (QC) method also was used as described previously (Thieme, et al., Quick and clean cloning: a ligation-independent cloning strategy for selective cloning of specific PCR products from non-specific mixes. PLoS One. 2011; 6(6):e20556. 16 µL, A1 vector (7.3 ng/µl), 1.5 µL, PCR product (47 ng/µl), 2 µL 10× T4 ligase buffer (NEB), and 0.5 µL, T4 DNA polymerase (NEB) were mixed and incubated in a PCR block for 60 min at 15° C.

Two microliters of Gibson assembly product was used to transform 100 mL of DH5a competent cells following a standard transformation protocol. The mini-preparation of plasmid DNAs was carried out using Zymo-Spin II columns (Zymo Research Corporation, Irvine, Calif.). Positive clones were identified by restriction enzyme digestion and sequencing.

Example 2

The donor vector was constructed from a BAC subclone based on homologous recombineering. A BAC subclone containing a 14.2 kb Lrba sequence was obtained from the BAC clone (RP24-352K5, from BACPAC Resources) by using the BAC Subcloning kit (Gene Bridges, Heidelberg, Germany) using primers Lrbasublow and Lrbasubup, seen in Table 2. A MluI enzyme site was introduced into the subclone by using the Quick & Easy Conditional Knockout Kit (Gene Bridges) and the primers MluIloxPF and MluIloxPR, seen in Table 2. Then, a CAG promoter with a STOP cassette was cloned into the MluI and ZraI sites. Subsequently, the neomycin gene flanked by Frt sites was inserted between the CAG promoter and the STOP cassette by using the Quick & Easy Conditional Knockout Kit with the selection cassette loxP-FRT-PGK-gb2-neo-FRT (Gene Bridges) and primers UpperFrt and LowerFrt. The resultant plasmid was then cleaved by PspXI and inserted into the RFP-P2A-rtTA cassette by using Quick and Clean Cloning (Thieme, et al., Quick and clean cloning: a ligation-independent cloning strategy for selective cloning of specific PCR products from non-specific mixes. PLoS One. 2011; 6(6):e20556). The tetracycline responsive element (TRE) was synthesized and cloned into the NotI site, and the first loxP site was cloned into the MluI site. Finally, a cyan fluorescent protein (CFP) gene with P2A sequences was inserted into the vector by CRISPR cloning (Tang, et al., Interaction of hsa-miR-381 and glioma suppressor LRRC4 is involved in glioma growth. Brain Res. 2011 May 16; 1390:21-32).

TABLE 2

Oligonucleotides used in generation of Lrba guide sequence for insertion into BAC subclone.

| Primer | Sequence | |
|---|---|---|
| Lrbasublow | SEQ ID No. 7 | TTTCTTGTTGCCATTTAATTTGTATCTATCTG ATATCAAGTCTTGGAATGCTCTCCTGAGTAGG ACAAATC |
| Lrbasubup | SEQ ID No. 8 | CATGTATTATGTATGCTCACATGTATAATTCC AAGTCTGGAGCTTGACATTCACAGCTTGTCTG TAAGCGGATG |
| MluIloxPF | SEQ ID No. 9 | TGCAGCGACTGCTGGCCCAGGGTGACTCTGAC TTGTCCTTTCTCGTGAacgcgtAATTAACCCT CACTAAAGGGCG |
| MluIloxPR | SEQ ID No. 10 | ACCTGTTGGTGGCCGGGAAGGGGCACGATTGT CTTCACTAGCCATGACTATAATACGACTCACT ATAGGGCTC |
| UpperFrt | SEQ ID No. 11 | ACGTGCTGGTTATTGTGCTGTCTCATCATTTT GGCAAAGAATTCCTCGAGAATTAACCCTCACT AAAGGGCG |
| LowerFrt | SEQ ID No. 12 | GTGATGCTATTGCTTTATTTGTAACCATTATA AGCTGCAATAAACAAGTTTAATACGACTCACT ATAGGGCTC |

Since antibiotic selection is not necessary in embryo targeting, the SW105 bacteria strain was used to remove the neomycin expression cassette between the two Frt sites in the donor vector by Flpe recombination (Warming, et al., Simple and highly efficient BAC recombineering using galK selection. Nucleic Acids Res. 2005 Feb. 24; 33(4):e36), reducing the insert size to 5.8 kb. The resultant Lrba donor vector and its intermediates were characterized by restriction digestion and then confirmed by sequencing. The digestion patterns are as expected for both donor vectors (with and without neomycin), shown in Table 3.

TABLE 3

Predicted plasmid DNA fragments digested by restriction enzyme

| pLrbaCNRTA (donor vector with neomycin). Size: 22446 bp | | | pLrbaCRTA (donor vector without neomycin). Size: 20896 bp | | |
|---|---|---|---|---|---|
| Fragments | Coordinates | Length (bp) | Fragments | Coordinates | Length (bp) |
| EcoRI | | | EcoRI | | |
| 1 | 16619-9260 | 15088 | 1 | 15069-11086 | 16914 |
| 2 | 9261-12636 | 3376 | 2 | 12565-15068 | 2504 |
| 3 | 14115-16618 | 2504 | 3 | 11087-12564 | 1478 |
| 4 | 12637-14114 | 1478 | | | |
| HindIII | | | HindIII | | |
| 1 | 12418-2688 | 12717 | 1 | 10868-2688 | 12717 |
| 2 | 7770-12417 | 4648 | 2 | 3810-7769 | 3960 |
| 3 | 3810-7769 | 3960 | 3 | 7770-10867 | 3098 |
| 4 | 2689-3809 | 1121 | 4 | 2689-3809 | 1121 |

TABLE 3-continued

Predicted plasmid DNA fragments digested by restriction enzyme

| pLrbaCNRTA (donor vector with neomycin). Size: 22446 bp | | | pLrbaCRTA (donor vector without neomycin). Size: 20896 bp | | |
|---|---|---|---|---|---|
| Fragments | Coordinates | Length (bp) | Fragments | Coordinates | Length (bp) |
| PvuII | | | PvuII | | |
| 1 | 19435-2773 | 5785 | 1 | 4531-10524 | 5994 |
| 2 | 13186-18850 | 5665 | 2 | 17885-2773 | 5785 |
| 3 | 4531-8642 | 4112 | 3 | 11636-17300 | 5665 |
| 4 | 8643-12074 | 3432 | | | |
| 5 | 2774-4356 | 1583 | 4 | 2774-4356 | 1583 |
| 6 | 12075-13185 | 1111 | 5 | 10525-11635 | 1111 |
| 7 | 19049-19434 | 386 | 6 | 17499-17884 | 386 |
| 8 | 18851-19048 | 198 | 7 | 17301-17498 | 198 |
| 9 | 4357-4416 | 60 | 8 | 4357-4416 | 60 |
| 10 | 4471-4530 | 60 | 9 | 4471-4530 | 60 |
| 11 | 4417-4470 | 54 | 10 | 4417-4470 | 54 |

Figure 1:
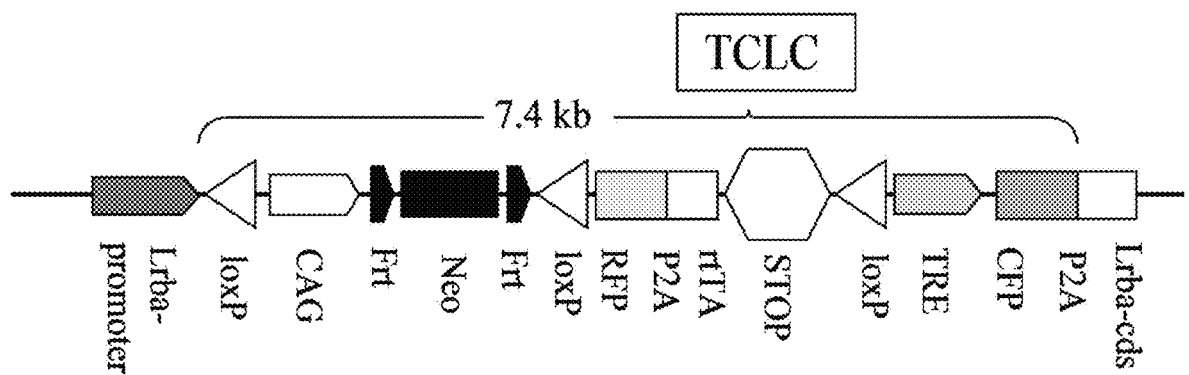
FIG. 1 is a diagram of the transcription control and labeling cassette (TCLC) used for the Lrba locus in mouse ES cells through CRISPR/HDR technique. Lrba-p, Lrba promoter; Triangles: loxP, locus of cross P1 site; STOP, three different polyadenylation signal sites for transcription termination and polyadenylation of mRNA; rtTA, reverse tetracycline controlled transcriptional activator, TRE, tetracycline responsive element.
Figure 2:
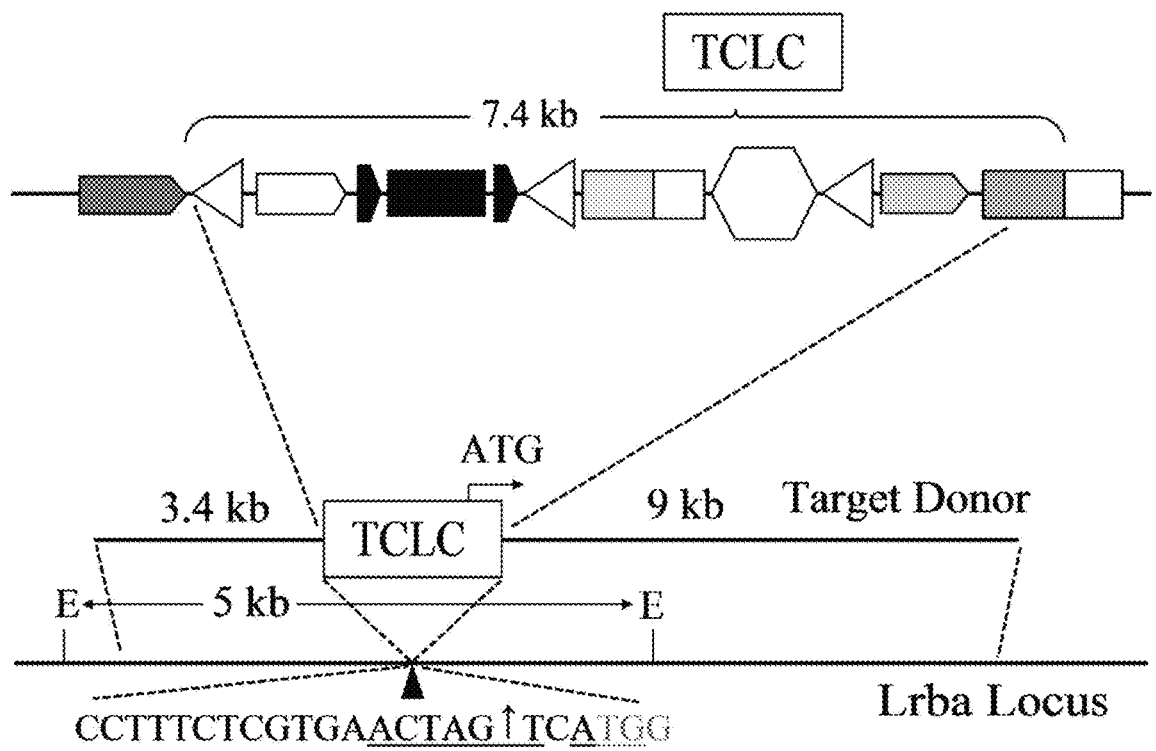
FIG. 2 is a diagram showing the strategy to knock-in a transcription control and labeling cassette (TCLC) (SEQ ID NO:28) into the Lrba locus in mouse ES cells through CRISPR/HDR technique. The sgRNA sequence is in black, and the protospacer-adjacent motif (PAM) sequence (NGG) is in gray. The underlined sequences are SpeI cleavage site and the translation start codon of Lrba. The cleavage site of Cas9 nuclease is indicated by an arrow. The sgRNA will guide the Cas9 nuclease to the target site and cleave the DNA. Homology directed repair (HDR) by the left and right arms (black bars) of the target donor will then insert the TCLC into the Lrba locus between the promoter and the Lrba translation start codon (ATG). E, EcoRV. Lrba-p, Lrba promoter; Triangles: loxP, locus of cross P1 site; STOP, three different polyadenylation signal sites for transcription termination and polyadenylation of mRNA; rtTA, reverse tetracycline controlled transcriptional activator, TRE, tetracycline responsive element.
Figure 3:
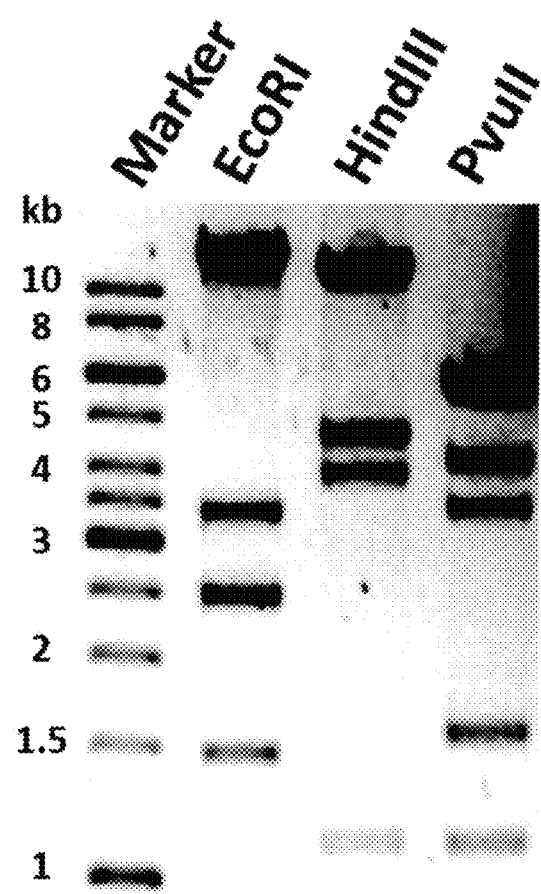
FIG. 3 is a blot showing the construction of Lrba CRISPR donor vectors. The target vector is constructed from a 12.5 kb genomic fragment. The TCLC splits the genomic fragment into 3.5 kb left and 9 kb right arms. The cloning of Lrba CRISPR donor vectors were characterized by agrose gel electrophoresis of restriction enzyme-digested plasmid DNAs. Lrba CRISPR donor vectors with neomycin gene (pLrbaCNRTA) were digested with the same set of restriction enzymes. The predicted fragments are shown in Table 3.
Figure 4:
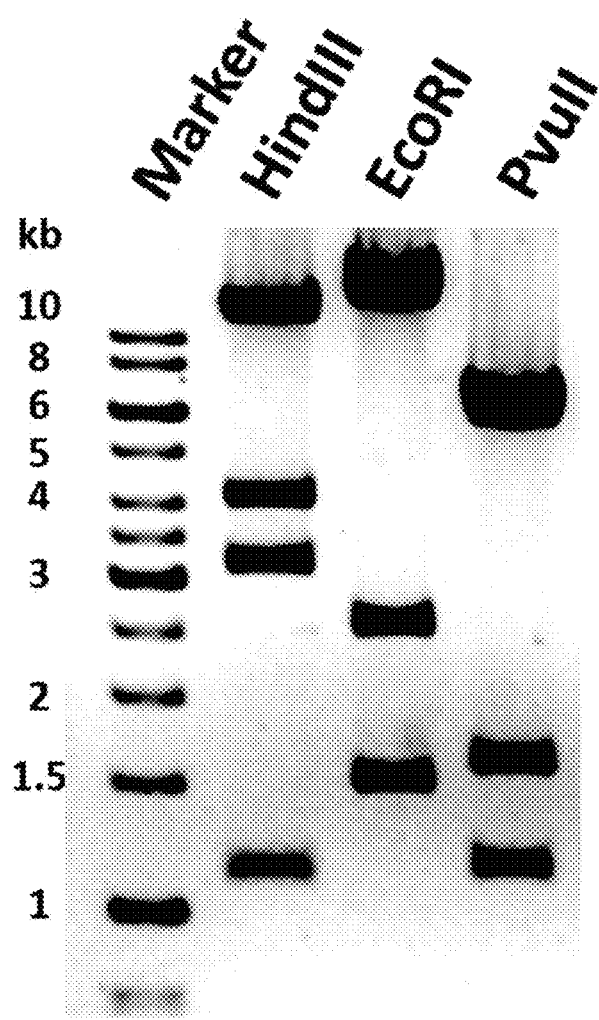
FIG. 4 is a blot showing the construction of Lrba CRISPR donor vectors. The target vector is constructed from a 12.5 kb genomic fragment. The TCLC splits the genomic fragment into 3.5 kb left and 9 kb right arms. The cloning of Lrba CRISPR donor vectors were characterized by agrose gel electrophoresis of restriction enzyme-digested plasmid DNAs. Lrba CRISPR donor vectors with without neomycin gene (pLrbaCRTA) were digested with the same set of restriction enzymes. The predicted fragments are shown in Table 3.

A 7.4 kb transcription control and labeling cassette (TCLC), seen in FIG. 1, was integrated at the Lrba genomic locus in mice, seen in FIG. 2. A donor Lrba vector was constructed from a BAC subclone, had homologous arms of 3.4 kb and 9 kb flanking the TCLC, and was characterized by restriction digestion, seen in FIGS. 3 and 4, and then confirmed by sequencing, as seen in Table 4.

TABLE 4

Sequence information from digested CRISPR donor vectors. Portions of sequencing show the sequences at the first loxP site 5' junction, the second loxP site, and the third loxP site 3' junction of the TCLC insertion.

| SEQ ID No. 13 | TTTCTCCGTGAACGCG<u>TCTTCAGGGTGAGTTT</u>ATAACTTCGTA TAATGTATGCTATACGAAGTTATACGCGTTGACATTGATTA* |
| --- | --- |
| SEQ ID No. 14 | ACCGGCGGCTCTAGTCGACTCGCGAGGCCGCATAACTTCGTAT AATGTATGCTATACGAAGTTATAAGCT† |
| SEQ ID No. 15 | GCTCTAGGGGGTATCCCCACGTAATACGACTCACTATAGGGCT CGAGATAACTTCGTATAATGTATGCTATACGAAGTTATGC‡ |

*Amino acids 490-570; first 10 amino acids are the 5' end of Lrba; underlined sequence is splice donor rabbit β globin; bold sequence is loxP-1; last 10 amino acids are 3' end of CAG
†Amino acids 20-190; first 10 amino acids are the 5' end of CAG; bold sequence is loxP-2
‡Amino acids 790-870; first 10 amino acids are the 5' end of BGH polyA; bold sequence is loxP-3

Example 3

The mouse ES cell line (JM8A3-N1, passage 7) was purchased from the Mouse Biology Program (MBP) at the University of California Davis. ES cells were grown on gelatin-treated cell culture plates with mitomycin-treated feeder cells (PMEF; neo resistant) at $2.5 \times 10^6$ cells per 10 cm plate using Dulbecco's modified Eagle's medium (DMEM), which contains 20% ES cell qualified fetal bovine serum (FBS), 0.1 mM 2-mercaptoethanol, MEM nonessential amino acids, and 1000 U recombinant murine leukemia inhibitory factor/mL (Millipore, Billerica, Mass.).

Example 4

Knockout ES cell clones were formed to test HDR-mediated gene targeting of mouse ES cells. To generate knockout ES cell clones, ES cells were cultured as described in Example 3. The cells were subcultured and $1 \times 10^7$ cells suspended in 0.9 mL 1×PBS, and the cells electroporated with 7.5 mg of single guide RNA (sgRNA) vector, described in Example 1. The electroporation was performed using the BioRad Gene Pulser II (Bio-Rad Laboratories, Hercules, Calif.) with the following settings: 250 mV, 500 mF capacitance. The ES cells were cultured with 500 mg/mL G418 for ~20 days. The G418-resistant colonies were picked and cultured in a 96-well plate until most wells were ~80% confluent with cells. The cells were then trypsinized and split into two 96-well plates. One plate of ES cells was frozen at −80° C., and another plate was used to prepare genomic DNA for PCR screening and confirmation by Southern blotting.

Example 5

Knock-in ES cell clones were formed to test HDR-mediated gene repair of mouse ES cells. Knock-in ES cell clones were formed by electroporating ES cells ($1 \times 10^7$ cells in 0.9 mL PBS) with sgRNA vector and donor vector, discussed in Examples 1 and 2. The cells were electroporated with 15 mg of linearized donor vector and 7.5 mg of single guide RNA sgRNA vector, using the BioRad Gene Pulser II (Bio-Rad Laboratories, Hercules, Calif.) with the following settings: 250 mV, 500 mF capacitance. The ES cells were cultured with 500 mg/mL G418 for ~20 days. The G418-resistant colonies were picked and cultured in a 96-well plate until most wells were ~80% confluent with cells. The cells were then trypsinized and split into two 96-well plates. One plate of ES cells was frozen at −80° C., and another plate was used to prepare genomic DNA for PCR screening and confirmation by Southern blotting.

To screen knock-in-positive ES cell clones by PCR, the primers mLALF and mLALR, seen in Table 5, were designed from the mouse genomic sequence immediately outside of the left homologous arm and the CAG promoter in the target vector, respectively, seen in FIG. 5 as P1 and P2. The fragment was amplified by PCR in a 20 ml reaction mixture composed of 4 ml 5× PrimeSTAR (Clontech Laboratories, Mountain View, Calif.) GXL buffer, 1.6 ml 2.5 mM dNTP mix, 0.4 ml 10 mM forward and reverse primers, 1 ml ES cell DNA from the 96-well preparation, 0.4 ml DMSO, and 0.4 ml PrimeSTAR GXL DNA polymerase (5 U/ml). Sterile distilled water was added to bring the total reaction volume to 20 ml. The PCR cycling parameters were: 98° C. for 5 min; 5 cycles of 94° C. for 10 s and 75° C. for 3 min 30 s; 5 cycles of 98° C. for 10 s and 72° C. for 3 min 30 s; 26 to 30 cycles of 98° C. for 10 s and 69.4° C. for 3 min 30 s; and 1 cycle of 72° C. for 10 min.

TABLE 5

Oligonucleotide primers and probes used in screening of knock-in-positive ES cell clones.

| Primer | | Sequence |
| --- | --- | --- |
| mLALF | SEQ ID No. 16 | GCAACAAGAAACTGGAACCTGGCTTTG (from sequence outside of the left homologous arm) |
| mLALR | SEQ ID No. 17 | CAGGCGGGCCATTTACCGTAAGTTAT (from CAG) |
| LAFWD1 | SEQ ID No. 18 | TGAGGAGGAACTTTGGACCTCAG (5' upstream of the targeting site) |

TABLE 5-continued

Oligonucleotide primers and probes used in
screening of knock-in-positive ES cell clones.

| Primer | | Sequence |
|---|---|---|
| LAREV1 | SEQ ID No. 19 | CACTTCTCCAACTTCAACCAACCC (3' downstream of the targeting site) |
| LrbaprbF | SEQ ID No. 20 | GGATGGCCTTCTGCTTAAT |
| LrbaprbR | SEQ ID No. 21 | ATTAGTTAGATCTAATGAAAGTTAGTCTA |
| loxP3F | SEQ ID No. 22 | TTCTGAGGCGGAAAGAACC |
| loxP3R | SEQ ID No. 23 | CACTGATAGGGAGTAAACTCTGG |
| loxPProbe | SEQ ID No. 24 | [6-FAM]ATAACTTCGTATAGCATACATTAT ACGAAGTTAT[BHQ1a-6FAM] |

To detect the presence of the wild-type (WT) allele, the primers LAFWD1 and LAREV1, seen in Table 5, that are located upstream and downstream of the targeting site, respectively, were designed from the mouse genomic sequence. The PCR conditions were the same as the above except for the PCR cycling parameters, which were: 98° C. for 5 min; 5 cycles of 98° C. for 10 s and 72° C. for 1 min; 5 cycles of 98° C. for 10 s and 69° C. for 1 min; 30 cycles of 98° C. for 10 s and 66° C. for 1 min; and 1 cycle of 72° C. for 10 min. PCR products (15 ml) were digested with 5 units of SpeI (NEB, Ipswich, Mass.) and 3 ml of CutSmart buffer in a total volume of 45 ml at 37° C. for 4 h.

The 3' end integrity of the knock-in was examined by detecting the presence of the third loxP sequence using Taqman real-time PCR with primers loxP3F and loxP3R and dual-labeled Taqman probe loxPProbe, seen in Table 5. One microliter genomic DNA was used for real-time PCR. All reactions were run on the CFX96 Real-Time System (Bio-Rad Laboratories) in 20 ml reactions using Premix Ex Taq (Probe qPCR) (Clontech Laboratories) with 10 mM primers and probe. The PCR cycling parameters were: 95° C. for 30 s, followed by 40 cycles of 95° C. for 5 s and 60° C. for 30 s. The baselines and quantification cycle (Cq) were set automatically.

The PCR generated from each clone was run on an agarose gel, as seen in FIGS. 6-10. It was observed that 67% of G418-positive ES cell clones were correctly targeted for the 5' HR, while more than 82% of G418-positive clones also had the third loxP sequence (loxP3) as seen in FIGS. 10 and 11, the presence of which may be an indication of the integrity of the 3' end of the insert. The clones that were positive for both 5'-recombination and the third loxP sequence have likely been correctly targeted.

Southern blotting was performed using standard methods to confirm knock-in-positive ES cell clones. The DNA probe was prepared with the PCR DIG Probe Synthesis Kit (Roche Diagnostics, Risch, Switzerland) by using the donor vector as the template with the primers LrbaprbF and LrbaprbR, seen in Table 5. Ten micrograms of genomic DNA were digested with EcoRV overnight and run on a 0.7% agarose gel. The DNA was transferred to a nylon membrane and hybridized with a digoxigenin-labeled probe. After stringent washing, the membrane was incubated with alkaline phosphatase-conjugated anti-digoxigenin antibodies (#11093274910; Roche Diagnostics). The chemiluminescent detection of positive signal on the membrane was achieved by incubation with CSPD (a chemiluminescent substrate for alkaline phosphatase) and developed on an X-ray film.

Since PCR approaches cannot detect concurrent random integration, Southern blotting was used to confirm the presence of the TCLC. It was observed that 70% of clones were correctly targeted based on the Southern blot, as seen in FIG. 12. This high CRISPR/HDR-mediated knock-in efficiency obtained in ES cells encouraged in vivo testing.

Example 6

Efficacy in an in vivo model was determined through microinjection of mouse zygotes with the CRISPR reagents. The HDR donor vector was derived from the targeting vector by removing the neomycin expression cassette, which reduced the insert size to 5.8 kb. The Cas9 mRNA was purchased from TriLink BioTechnologies (San Diego, Calif.). The sgRNA targeting the mouse lipopolysaccharide responsive vesicle trafficking, beach and anchor containing (Lrba) gene was synthesized in vitro from the PCR products of the pX330-LAsg vector as described above. The 3 CRISPR components were mixed in microinjection buffer (10 mM Tris-HCl pH 7.4, 0.25 mM EDTA) at concentrations of 5 ng/µl Cas9, 2.5 ng/µl sgRNA, and 10 ng/µl donor DNA vector, and were microinjected into the pronucleus at the University of Michigan Transgenic Animal Model Core. Positive control CRISPR reagents were also microinjected into fertilized eggs of the same genetic background under the same conditions and then incubated to follow the in vivo development of microinjected eggs through the blastocyst stage. Uninjected eggs were placed in culture in parallel under the same conditions to determine if medium and incubator conditions were optimal. Animals were housed in an AAALAC accredited facility in accordance with the National Research Council's guide for the care and use of laboratory animals.

Knock-in genes in blastocysts were screened using nested PCR. Each blastocyst derived from a zygote injected with CRISPR reagents was put into 10 ml water and stored at −80° C. To extract blastocyst genomic DNA, 10 ml 2× digestion buffer (100 mM KCl, 20 mM Tris-HCl pH 9.0, 0.2% Triton X-100, and 0.8 mg/mL proteinase K) were added into each tube containing 1 blastocyst and incubated at 55° C. overnight, followed by incubation at 94° C. for 10 min to inactivate the proteinase K. Five microliters of the blastocyst DNA preparation were used as PCR template for the first PCR reaction using the same conditions and parameters as the PCR screening of knock-in-positive ES cell clones, with the exception that the number of cycles in the third phase of the touchdown PCR program was changed to 20. The second (nested) PCR reactions were conducted as follows: the nested PCR primers are LAFWD1 and FL30R, seen in Table 6, and the PCR conditions were the same as the above except for the cycling parameters, which were: 98° C. for 5 min; 5 cycles of 98° C. for 10 s and 69.5° C. for 1 min; 5 cycles of 98° C. for 10 s and 66.5° C. for 1 min; 28 cycles of 98° C. for 10 s and 63.5° C. for 1 min; and 1 cycle of 72° C. for 10 min.

TABLE 6

Oligonucleotides primers used in nested PCR
for screening of knock-in-positive Lrba.

| Primer | | Sequence |
|---|---|---|
| LAFWD1 | SEQ ID No. 18 | TGAGGAGGAACTTTGGACCTCAG (from Lrba) |
| FL30R | SEQ ID No. 25 | AACTAGTCAATAATCAATGTCAACGCGTAT (from CAG and loxP) |

As noted in Example 5, the high CRISPR/HDR-mediated knock-in efficiency obtained in ES cells prompted testing for similar efficiencies in vivo, in particular in mouse zygotes. The CRISPR reagents injected at the regular concentrations (Yang, et al., One-step generation of mice carrying reporter and conditional alleles by CRISPR/Cas-mediated genome engineering. Cell. 2013 Sep. 12; 154(6):1370-9) interfered with the normal development of zygotes. Only 9% of zygotes injected with the CRISPR reagents developed into blastocysts, as seen in Table 7. To reduce this toxicity, the reagents were diluted 4-fold. The diluted reagents produced the best results when compared with the positive controls with or without the DNA ligase IV inhibitor Scr7, which inhibits NHEJ, as seen in Table 7.

TABLE 7

Fertilized mouse egg development after Cas9 treatment.

| Cas9 DNA construct | Injected eggs | Intact eggs (average ± SD) | 2-cell eggs (average ± SD) | blastocysts (average ± SD) |
|---|---|---|---|---|
| Lrba/Cas9 diluted* | 60 | 54 (90 ± 0.0%) | 52 (87 ± 0.0%) | 37 (62 ± 0.7%) |
| Lrba/Cas9* | 60 | 38 (60 ± 0.9%) | 31 (74 ± 3.7%) | 3 (9 ± 13%) |
| control† | 93 | 82 (88 ± 2.3%) | 56 (60 ± 1.7%) | 5 (6 ± 0.2%) |
| control + Scr7 | 32 | 25 (78%) | 21 (66%) | 12 (38%) |
| no injection' | N/A | 60 (100 ± 0.0%) | 60 (100 ± 0.0%) | 58 (97 ± 2.9%) |

Two (*) or three (†) biological replicates. N/A = not applicable; SD = standard error.

Nested-PCR genotyping revealed that the targeting efficiency for mouse zygotes was 32%, seen in FIG. 13. This frequency would have been higher if the regular concentrations of CRISPR reagents had been used. High efficiency of HDR-mediated knock-in in mice is expected as the CRISPR knockout efficiencies are almost the same in ES cells and mice (Wang, et al., One-Step Generation of Mice Carrying Mutations in Multiple Genes by CRISPR/Cas-Mediated Genome Engineering. Cell. 2013 May 9; 153(4):910-8). The advantages of using lower concentrations of CRISPR reagents may include lower toxicity, lower off-target rates, and lower cost. Evidence of genome editing in blastocysts indicated that genome-edited mice could be produced. 311 embryos were injected with the diluted CRISPR reagents and obtained a survival rate of 82% for the blastocysts, which were transferred to pseudopregnant recipients. A 34% birth rate (86 pups) was obtained. The high survival rate of blastocysts and the high birth rate support the use of low concentrations of CRISPR reagents.

The high efficiency of CRISPR/HDR, shown in Table 8, without NHEJ inhibitors suggests that long homologous arms (3.2 and 7.6 kb), which are much longer than the recommended 800 bp (Yang, et al., One-step generation of mice carrying reporter and conditional alleles by CRISPR/Cas-mediated genome engineering. Cell. 2013 Sep. 12; 154(6):1370-9), are required to obtain high knock-in efficiency (Song, et al., Modeling disease in human ESCs using an efficient BAC-based homologous recombination system. Cell Stem Cell. 2010 Jan. 8; 6(1):80-9).

TABLE 8

Targeting efficiency of CRISPR/HDR in ES cells and zygotes

| Embryonic Stem (ES) cells | | | Zygotes |
|---|---|---|---|
| Southern blot | PCR | real-time PCR | PCR |
| 7/10 (70%) | 41/60 (67%) | 27/33 (82%) | 6/19 (32%) |

The frequency of traditional gene targeting is roughly proportional to the extent of homology shared by the transgene and its target locus (Smith, Theoretical mechanisms in targeted and random integration of transgene DNA. Reprod Nutr Dev. 2001 November-December; 41(6):465-85). For example, a 40-fold increase in the rate of targeting has been observed with an increase in homology from 4 kb to 9.1 kb (Thomas & Capecchi, Site-directed mutagenesis by gene targeting in mouse embryo-derived stem cells. Cell. 1987 November; 51(3):503-12). A 25-fold increase was seen over the range of 2.5 kb to 9.5 kb of homology (Shulman, et al., Homologous recombination in hybridoma cells: dependence on time and fragment length. Mol Cell Biol. 1990 September; 10(9):4466-72). A parallel comparison of targeting efficiency of two targeting vectors with different lengths of homologous arms flanking the same insert were conducted, seen in Table 9.

TABLE 9

Generation of HDR repair templates with long or short homologous arms by digesting the donor vector with restriction enzymes.

| Fragments | Ends | Coordinates | Length (bp) | Fragments | Ends | Coordinates | Length (bp) |
|---|---|---|---|---|---|---|---|
| Repair template with long homologous arms | | | | Repair template with short homologous arms | | | |
| Left arm | BglII-Left | 2844-6032 | 3188 | Left arm | BglII-Left | 3890-6032 | 2142 |
| Insert | Left-Right | 6032-13435 | 7403 | Insert | Left-Right | 6032-13435 | 7403 |
| Right arm | Right-BglII | 13435-21008 | 7573 | Right arm | Right-EcoRV | 13435-15099 | 1664 |

Left, Right: left- and right-ends of the insert.

Although there is total of ~7 kb difference of the homologous sequences between the 2 targeting vectors, the results show that there is no obvious difference in targeting efficiency between the 2 targeting vectors, seen in FIG. 14. This indicates that the targeting efficiency of CRISPR/HDR is not dependent on the lengths of each homologous arm in the range of 1.7 kb to 7.6 kb, and that increasing the length of each homologous arm in this range may not increase the CRISPR/HDR targeting efficiency as it does for traditional gene targeting. Our results also show that a —2 kb homologous arm at each end should be sufficient for CRISPR/HDR, and it can be easily obtained by PCR amplification, thus making it easier to construct a targeting vector. Although extremely short (50 bp) homologous arms of double-stranded DNA can mediate HDR at 5%-10% efficiency, they may not efficiently mediate HDR of a larger insert such as the 7.4 kb fragment used in this study (Orlando, et al., Zinc-finger nuclease-driven targeted integration into Mamm. Genomes using donors with limited chromosomal homology. Nucleic Acids Res. 2010 August; 38(15):e152). Indeed, increasing the insert length from 99 bp to 720 bp considerably reduced targeting efficiency (9-fold), but that can be compensated for by increasing the homology arm size (Li, et al., Optimization of genome engineering approaches with the CRISPR/Cas9 system. PLoS One. 2014 August 28; 9(8):e105779). Increasing the lengths of homologous arms in the range of 50 bp to 2 kb likely increases the targeting efficiency.

While high CRISPR/HDR gene targeting efficiency was obtained for both ES cells and zygotes, no biallelic knock-ins were detected by Southern blotting and PCR screening in ES cells. It is possible that the mutated alleles may have NHEJ-mediated small insertion/deletion (indel) mutations that cannot be distinguished from the WT alleles by the two methods used above. These mutations would destroy the SpeI site, seen in FIG. 15, in the Cas9/sgRNA recognition site, since the Cas9/sgRNA complex cleaves 3-8 nucleotides upstream of the protospacer adjacent motif (PAM) (Jinek, et al., A programmable dual-RNA-guided DNA endonuclease in adaptive bacterial immunity. Science. 2012 August 17; 337(6096):816-21; Li, et al., A versatile reporter system for CRISPR-mediated chromosomal rearrangements. Genome Biol. 2015 May 28; 16:111; Doudna & Charpentier, Genome editing. The new frontier of genome engineering with CRISPR-Cas9. Science. 2014 November 28; 346(6213): 1258096), and this SpeI site is located just within the cleavage range. Although the feeder cells contribute to the PCR products, their numbers in each culture well were ~20 times less than that of ES cells. Therefore, the PCR products should mainly originate from the ES cells. SpeI digestion can thus be used to detect NHEJ-induced mutations. In a CRISPR/NHEJ experiment, SpeI can digest the PCR product (713 bp) from the WT allele, producing 527 bp and 186 bp fragments, but it cannot cut the CRISPR-mutated allele as the SpeI site would be destroyed by the CRISPR mutation, seen in FIG. 15. However, in the CRISPR/HDR experiments, all PCR products were digested by SpeI, seen in FIG. 16; there was no uncleaved band for any clone among the 41 targeted clones and the 19 non-targeted clones. These results indicate that all of these clones have at least one WT allele, but there are no mutated alleles resulting from CRISPR/NHEJ, while this Cas9/sgRNA system can completely cleave its substrate in vitro (Wang, et al., CRISPR/Cas9 nuclease cleavage combined with Gibson assembly for seamless cloning. Biotechniques. 2015 April 1; 58(4):161-70) and successfully mutated the target site in ES cells at the absence of a donor vector, seen in FIG. 15.

This is a surprising result given that the frequency of CRISPR/NHEJ mutations is usually higher than that of CRISPR/HDR (Wang, et al., One-Step Generation of Mice Carrying Mutations in Multiple Genes by CRISPR/Cas-Mediated Genome Engineering. Cell. 2013 May 9; 153(4): 910-8; Yang, et al., One-step generation of mice carrying reporter and conditional alleles by CRISPR/Cas-mediated genome engineering. Cell. 2013 September 12; 154(6): 1370-9). NHEJ occurs throughout the cell cycle, while HDR occurs only during the S and G2 phases (Maruyama, et al., Increasing the efficiency of precise genome editing with CRISPR-Cas9 by inhibition of nonhomologous end joining. Nat. Biotechnol. 2015 May; 33(5):538-42). These two repair pathways seem to compete for DSBs, and inhibiting NHEJ significantly increases the efficiency of HDR (Maruyama, et al., Increasing the efficiency of precise genome editing with CRISPR-Cas9 by inhibition of nonhomologous end joining. Nat. Biotechnol. 2015 May; 33(5):538-42; Chu, et al., Increasing the efficiency of homology-directed repair for CRISPR-Cas9-induced precise gene editing in mammalian cells. Nat. Biotechnol. 2015 May; 33(5):543-8). On the other hand, the CRISPR/Cas9 cleavage site is restored and can be cleaved again after complete repair of a DSB by NHEJ. This cycle of cleavage/NHEJ-repair may be repeated multiple times until the DSB is repaired with a mutation. However, once a DSB is repaired by HDR and a donor DNA fragment is inserted, the CRISPR/Cas9 cleavage site is destroyed and cannot be cleaved again by CRISPR/Cas9 (Singh, et al., A mouse geneticist's practical guide to CRISPR applications. Genetics. 2015 January; 199(1):1-15). In this sense, CRISPR/HDR is more efficient than CRISPR/NHEJ, which may require multiple rounds of cleavage/repair. In this study, it is possible that the NHEJ repairs almost all of the DSB sites at this genomic site without mutation, or that the NHEJ-mediated mutations are inhibited by some unknown mechanisms. As for no biallelic knock-ins being detected, it is likely that the double knock-in is lethal to the cells because knockdown of Lrba induces apoptosis (Wang, et al., Deregulated expression of LRBA facilitates cancer cell growth. Oncogene. 2004 May 20; 23(23):4089-97). Since whether cells choose NHEJ or HDR is fundamental to CRISPR/Cas9 gene targeting, further investigation of these surprising results is warranted.

Another intriguing observation is that most of the G418-positive clones resulted from HR. This result is in sharp contrast to the traditional targeting, where most of the G418-positive clones result from random integration. The frequency of random integration is typically 1000 times more than that of targeted integration (Smith, Theoretical mechanisms in targeted and random integration of transgene DNA. Reprod Nutr Dev. 2001 November-December; 41(6): 465-85). These results indicate that by increasing DNA DSBs at the correct site, CRISPR favors on-target integration as opposed to random integration.

It was demonstrated that (i) the targeting efficiency of CRISPR/HDR without using any NHEJ inhibitors is equivalent to that of CRISPR/HDR with NHEJ inhibitors; (ii) CRISPR/NHEJ is not detectable; (iii) biallelic knock-in is not detectable; (iv) left and right homologous arms longer than 2.1 and 1.7 kb, respectively, do not increase HDR efficiency; (v) one fourth of the regular concentrations of CRISPR reagents can be used to knock in a large DNA fragment into the genome of mouse zygotes at high efficiency with low toxicity; and (vi) large DNA fragments, 7.4 and 5.8 kb, can be knocked in to the genomes of ES cells and zygotes, respectively. These results should inspire interest in further study of the mechanisms of high CRISPR targeting efficiency, as well as provide an example of how to obtain high efficiency gene knock-in results with large DNA fragments using CRISPR/HDR without the need for NHEJ inhibitors.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments herein, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A method of genome editing to knock in a large DNA fragment into a target gene of a host in the absence of a non-homologous end joining (NHEJ) inhibitor, comprising:
   providing at least one clustered regularly interspaced short palindromic repeat (CRISPR) system comprising
      a first plasmid nucleic acid vector comprising
         a DNA encoding a single guide RNA (sgRNA) wherein the single guide RNA comprising
            a CRISPR-related (crRNA) segment complementary to a target sequence in the target gene of the host; and
            a trans-activating CRISPR-related sequence (tracrRNA) required for function of a CRISPR endonuclease; and
         a DNA encoding the CRISPR endonuclease wherein the CRISPR endonuclease is Cas9;
      a second plasmid nucleic acid vector comprising
         a donor DNA sequence comprising
            a DNA fragment of at least 4 kb in length wherein the DNA fragment replaces the target sequence in the target gene of the host or is inserted into a target site in the target gene of the host; and
            two homologous arms with each arm flanking opposing sides of the DNA fragment wherein each of the homologous arms is between 3.4 kb and 9 kb in size;
   inserting the at least one CRISPR system into a cell wherein the sgRNA guides the CRISPR endonuclease to a cleavage site in the target DNA sequence of the target gene of the host and the CRISPR endonuclease introduces a double stranded break in the target DNA sequence in the target gene of the host; and
   allowing the cell to undergo homology-directed-repair using the two homologous arms flanking the DNA fragment to knock in the DNA fragment at the cleavage site of the target DNA sequence in the target gene of the host in the absence of a non-homologous end joining (NHEJ) inhibitor.

2. The method of claim 1, wherein a concentration of the sgRNA, of the CRISPR endonuclease, and the donor DNA is about one fourth of a standard concentration.

3. The method of claim 1, wherein the at least one CRISPR system is inserted into the cell by electroporation or microinjection.

4. The method of claim 3, wherein the CRISPR insertion further comprises:
   providing a microinjection buffer;
   mixing the CRISPR system in the microinjection buffer to form a microinjection solution; and
   injecting the microinjection solution into the cell.

5. The method of claim 4, wherein the cell is a zygote or stem cell.

6. A method of genome editing to knock in a large DNA fragment into a target gene of a host in the absence of a non-homologous end joining (NHEJ) inhibitor, comprising:
   providing at least one clustered regularly interspaced short palindromic repeat (CRISPR) system comprising
      a first nucleic acid vector comprising
         a DNA encoding a single guide RNA (sgRNA); and
         a DNA encoding a CRISPR endonuclease;
      a second nucleic acid vector comprising
         a donor DNA sequence comprising
            a DNA fragment of at least 4 kb in length; and
            two homologous arms with each arm flanking opposing sides of the DNA fragment wherein each of the homologous arms is between 3.4 kb and 9 kb in size; and
   inserting the at least one CRISPR system into a cell; and
   allowing the cell to undergo homology-directed-repair using the two homologous arms flanking the DNA fragment to knock in the DNA fragment at a cleavage site in the target DNA sequence in the target gene of the host in the absence of the non-homologous end joining (NHEJ) inhibitor.

7. The method of claim 6, wherein a concentration of the sgRNA, of the CRISPR endonuclease, and the donor DNA is about one fourth of a standard concentration.

8. The method of claim 6, wherein the CRISPR endonuclease is Cas9 or Cpf1.

* * * * *

SEQUENCE LISTING

```
<160> NUMBER OF SEQ ID NOS: 28

<210> SEQ ID NO 1
<211> LENGTH: 25
<212> TYPE: DNA
<213> ORGANISM: artificial
<220> FEATURE:
<223> OTHER INFORMATION: sgRNA oligo- forward direction

<400> SEQUENCE: 1
caccgccttt ctcgtgaact agtca                                    25

<210> SEQ ID NO 2
<211> LENGTH: 25
<212> TYPE: DNA
<213> ORGANISM: artificial
<220> FEATURE:
<223> OTHER INFORMATION: sgRNA oligo-  reverse direction

<400> SEQUENCE: 2
aaactgacta gttcacgaga aaggc                                    25

<210> SEQ ID NO 3
<211> LENGTH: 20
<212> TYPE: DNA
<213> ORGANISM: artificial
<220> FEATURE:
<223> OTHER INFORMATION: guide RNA oligo

<400> SEQUENCE: 3
cctttctcgt gaactagtca                                          20

<210> SEQ ID NO 4
<211> LENGTH: 41
<212> TYPE: DNA
<213> ORGANISM: artificial
<220> FEATURE:
<223> OTHER INFORMATION: sgRNA LA target sequence- forward primer

<400> SEQUENCE: 4
tgtaatacga ctcactatag gcctttctcg tgaactagtc a                  41

<210> SEQ ID NO 5
<211> LENGTH: 20
<212> TYPE: DNA
<213> ORGANISM: artificial
<220> FEATURE:
<223> OTHER INFORMATION: sgRNA LA target sequence- reverse primer

<400> SEQUENCE: 5
aaaagcaccg actcggtgcc                                          20

<210> SEQ ID NO 6
<211> LENGTH: 60
<212> TYPE: DNA
```

<213> ORGANISM: artificial
<220> FEATURE:
<223> OTHER INFORMATION: sgRNA targeting the T3 promoter

<400> SEQUENCE: 6
tgtaatacga ctcactatag gctaaattaa ccctcactaa gttttagagc tagaaatagc      60

<210> SEQ ID NO 7
<211> LENGTH: 71
<212> TYPE: DNA
<213> ORGANISM: artificial
<220> FEATURE:
<223> OTHER INFORMATION: oligo for Lrba sequence

<400> SEQUENCE: 7
tttcttgttg ccatttaatt tgtatctatc tgatatcaag tcttggaatg ctctcctgag      60
taggacaaat c                                                          71

<210> SEQ ID NO 8
<211> LENGTH: 74
<212> TYPE: DNA
<213> ORGANISM: artificial
<220> FEATURE:
<223> OTHER INFORMATION: oligo for Lrba sequence

<400> SEQUENCE: 8
catgtattat gtatgctcac atgtataatt ccaagtctgg agcttgacat tcacagcttg      60
tctgtaagcg gatg                                                       74

<210> SEQ ID NO 9
<211> LENGTH: 76
<212> TYPE: DNA
<213> ORGANISM: artificial
<220> FEATURE:
<223> OTHER INFORMATION: oligo to generate MluI enzyme site- forward
      direction

<400> SEQUENCE: 9
tgcagcgact gctggcccag ggtgactctg acttgtcctt tctcgtgaac gcgtaattaa      60
ccctcactaa agggcg                                                     76

<210> SEQ ID NO 10
<211> LENGTH: 73
<212> TYPE: DNA
<213> ORGANISM: artificial
<220> FEATURE:
<223> OTHER INFORMATION: oligo to generate MluI enzyme site- reverse
      direction

<400> SEQUENCE: 10
acctgttggt ggccgggaag gggcacgatt gtcttcacta gccatgacta taatacgact      60
cactataggg ctc                                                        73

<210> SEQ ID NO 11
<211> LENGTH: 72
<212> TYPE: DNA
<213> ORGANISM: artificial
<220> FEATURE:
<223> OTHER INFORMATION: oligo to generate FRT site

<400> SEQUENCE: 11
acgtgctggt tattgtgctg tctcatcatt ttggcaaaga attcctcgag aattaaccct      60
cactaaaggg cg                                                         72

```
<210> SEQ ID NO 12
<211> LENGTH: 73
<212> TYPE: DNA
<213> ORGANISM: artificial
<220> FEATURE:
<223> OTHER INFORMATION: oligo to generate FRT site

<400> SEQUENCE: 12
gtgatgctat tgctttattt gtaaccatta taagctgcaa taaacaagtt taatacgact    60
cactataggg ctc                                                      73

<210> SEQ ID NO 13
<211> LENGTH: 84
<212> TYPE: DNA
<213> ORGANISM: artificial
<220> FEATURE:
<223> OTHER INFORMATION: digested generated Lrba vector

<400> SEQUENCE: 13
tttctccgtg aacgcgtctt cagggtgagt ttataacttc gtataatgta tgctatacga    60
agttatacgc gttgacattg atta                                          84

<210> SEQ ID NO 14
<211> LENGTH: 70
<212> TYPE: DNA
<213> ORGANISM: artificial
<220> FEATURE:
<223> OTHER INFORMATION: digested generated Lrba vector

<400> SEQUENCE: 14
accggcggct ctagtcgact cgcgaggccg cataacttcg tataatgtat gctatacgaa    60
gttataagct                                                          70

<210> SEQ ID NO 15
<211> LENGTH: 83
<212> TYPE: DNA
<213> ORGANISM: artificial
<220> FEATURE:
<223> OTHER INFORMATION: digested generated Lrba vector

<400> SEQUENCE: 15
gctctagggg gtatccccac gtaatacgac tcactatagg gctcgagata acttcgtata    60
atgtatgcta tacgaagtta tgc                                           83

<210> SEQ ID NO 16
<211> LENGTH: 27
<212> TYPE: DNA
<213> ORGANISM: artificial
<220> FEATURE:
<223> OTHER INFORMATION: oligo to screen for Lrba knock-in- forward

<400> SEQUENCE: 16
gcaacaagaa actggaacct ggctttg                                       27

<210> SEQ ID NO 17
<211> LENGTH: 26
<212> TYPE: DNA
<213> ORGANISM: artificial
<220> FEATURE:
<223> OTHER INFORMATION: oligo to screen for Lrba knock-in- forward

<400> SEQUENCE: 17
```
caggcgggcc atttaccgta agttat                                        26

<210> SEQ ID NO 18
<211> LENGTH: 23
<212> TYPE: DNA
<213> ORGANISM: artificial
<220> FEATURE:
<223> OTHER INFORMATION: oligo to detect Lrba wild type allele- forward

<400> SEQUENCE: 18
tgaggaggaa ctttggacct cag                                           23

<210> SEQ ID NO 19
<211> LENGTH: 24
<212> TYPE: DNA
<213> ORGANISM: artificial
<220> FEATURE:
<223> OTHER INFORMATION: oligo to detect Lrba wild type allele- reverse

<400> SEQUENCE: 19
cacttctcca acttcaacca accc                                          24

<210> SEQ ID NO 20
<211> LENGTH: 19
<212> TYPE: DNA
<213> ORGANISM: artificial
<220> FEATURE:
<223> OTHER INFORMATION: DNA probe directed to donor vector template-
      forward

<400> SEQUENCE: 20
ggatggcctt ctgcttaat                                                19

<210> SEQ ID NO 21
<211> LENGTH: 29
<212> TYPE: DNA
<213> ORGANISM: artificial
<220> FEATURE:
<223> OTHER INFORMATION: DNA probe directed to donor vector template-
      reverse

<400> SEQUENCE: 21
attagttaga tctaatgaaa gttagtcta                                     29

<210> SEQ ID NO 22
<211> LENGTH: 19
<212> TYPE: DNA
<213> ORGANISM: artificial
<220> FEATURE:
<223> OTHER INFORMATION: PCR primer directed to loxP sequence- forward

<400> SEQUENCE: 22
ttctgaggcg gaaagaacc                                                19

<210> SEQ ID NO 23
<211> LENGTH: 23
<212> TYPE: DNA
<213> ORGANISM: artificial
<220> FEATURE:
<223> OTHER INFORMATION: PCR primer directed to loxP sequence- reverse

<400> SEQUENCE: 23
cactgatagg gagtaaactc tgg                                           23

<210> SEQ ID NO 24
<211> LENGTH: 34

```
<212> TYPE: DNA
<213> ORGANISM: artificial
<220> FEATURE:
<223> OTHER INFORMATION: oligo portion of fluorescent probe directed to
      loxP sequence

<400> SEQUENCE: 24
ataacttcgt atagcataca ttatacgaag ttat                                   34

<210> SEQ ID NO 25
<211> LENGTH: 30
<212> TYPE: DNA
<213> ORGANISM: artificial
<220> FEATURE:
<223> OTHER INFORMATION: nested PCR primer directed to loxP and CAG-
      reverse

<400> SEQUENCE: 25
aactagtcaa taatcaatgt caacgcgtat                                        30

<210> SEQ ID NO 26
<211> LENGTH: 1368
<212> TYPE: PRT
<213> ORGANISM: Streptococcus pyogenes

<400> SEQUENCE: 26
```

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

```
Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
        290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
```

```
            675                 680                 685
Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
                835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
                930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
                995                1000                1005

Val Tyr Gly Asp Tyr Lys Val Tyr Asp Val Arg Lys Met Ile Ala
                1010                1015                1020

Lys Ser Glu Gln Glu Ile Gly Lys Ala Thr Ala Lys Tyr Phe Phe
                1025                1030                1035

Tyr Ser Asn Ile Met Asn Phe Phe Lys Thr Glu Ile Thr Leu Ala
                1040                1045                1050

Asn Gly Glu Ile Arg Lys Arg Pro Leu Ile Glu Thr Asn Gly Glu
                1055                1060                1065

Thr Gly Glu Ile Val Trp Asp Lys Gly Arg Asp Phe Ala Thr Val
                1070                1075                1080

Arg Lys Val Leu Ser Met Pro Gln Val Asn Ile Val Lys Lys Thr
                1085                1090                1095
```

```
Glu Val Gln Thr Gly Gly Phe Ser Lys Glu Ser Ile Leu Pro Lys
    1100            1105                1110

Arg Asn Ser Asp Lys Leu Ile Ala Arg Lys Lys Asp Trp Asp Pro
    1115            1120                1125

Lys Lys Tyr Gly Gly Phe Asp Ser Pro Thr Val Ala Tyr Ser Val
    1130            1135                1140

Leu Val Val Ala Lys Val Glu Lys Gly Lys Ser Lys Lys Leu Lys
    1145            1150                1155

Ser Val Lys Glu Leu Leu Gly Ile Thr Ile Met Glu Arg Ser Ser
    1160            1165                1170

Phe Glu Lys Asn Pro Ile Asp Phe Leu Glu Ala Lys Gly Tyr Lys
    1175            1180                1185

Glu Val Lys Lys Asp Leu Ile Ile Lys Leu Pro Lys Tyr Ser Leu
    1190            1195                1200

Phe Glu Leu Glu Asn Gly Arg Lys Arg Met Leu Ala Ser Ala Gly
    1205            1210                1215

Glu Leu Gln Lys Gly Asn Glu Leu Ala Leu Pro Ser Lys Tyr Val
    1220            1225                1230

Asn Phe Leu Tyr Leu Ala Ser His Tyr Glu Lys Leu Lys Gly Ser
    1235            1240                1245

Pro Glu Asp Asn Glu Gln Lys Gln Leu Phe Val Glu Gln His Lys
    1250            1255                1260

His Tyr Leu Asp Glu Ile Ile Glu Gln Ile Ser Glu Phe Ser Lys
    1265            1270                1275

Arg Val Ile Leu Ala Asp Ala Asn Leu Asp Lys Val Leu Ser Ala
    1280            1285                1290

Tyr Asn Lys His Arg Asp Lys Pro Ile Arg Glu Gln Ala Glu Asn
    1295            1300                1305

Ile Ile His Leu Phe Thr Leu Thr Asn Leu Gly Ala Pro Ala Ala
    1310            1315                1320

Phe Lys Tyr Phe Asp Thr Thr Ile Asp Arg Lys Arg Tyr Thr Ser
    1325            1330                1335

Thr Lys Glu Val Leu Asp Ala Thr Leu Ile His Gln Ser Ile Thr
    1340            1345                1350

Gly Leu Tyr Glu Thr Arg Ile Asp Leu Ser Gln Leu Gly Gly Asp
    1355            1360                1365

<210> SEQ ID NO 27
<211> LENGTH: 1300
<212> TYPE: PRT
<213> ORGANISM: Francisella novicida

<400> SEQUENCE: 27

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
                20                  25                  30

Ala Arg Gly Leu Ile Leu Asp Asp Glu Lys Arg Ala Lys Asp Tyr Lys
            35                  40                  45

Lys Ala Lys Gln Ile Ile Asp Lys Tyr His Gln Phe Phe Ile Glu Glu
        50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asp Asn Leu Gln Lys
```

```
                     85                  90                  95
Asp Phe Lys Ser Ala Lys Asp Thr Ile Lys Lys Gln Ile Ser Glu Tyr
                100                 105                 110
Ile Lys Asp Ser Glu Lys Phe Lys Asn Leu Phe Asn Gln Asn Leu Ile
                115                 120                 125
Asp Ala Lys Lys Gly Gln Glu Ser Asp Leu Ile Leu Trp Leu Lys Gln
                130                 135                 140
Ser Lys Asp Asn Gly Ile Glu Leu Phe Lys Ala Asn Ser Asp Ile Thr
145                 150                 155                 160
Asp Ile Asp Glu Ala Leu Glu Ile Ile Lys Ser Phe Lys Gly Trp Thr
                165                 170                 175
Thr Tyr Phe Lys Gly Phe His Glu Asn Arg Lys Asn Val Tyr Ser Ser
                180                 185                 190
Asn Asp Ile Pro Thr Ser Ile Ile Tyr Arg Ile Val Asp Asp Asn Leu
                195                 200                 205
Pro Lys Phe Leu Glu Asn Lys Ala Lys Tyr Glu Ser Leu Lys Asp Lys
                210                 215                 220
Ala Pro Glu Ala Ile Asn Tyr Glu Gln Ile Lys Lys Asp Leu Ala Glu
225                 230                 235                 240
Glu Leu Thr Phe Asp Ile Asp Tyr Lys Thr Ser Glu Val Asn Gln Arg
                245                 250                 255
Val Phe Ser Leu Asp Glu Val Phe Glu Ile Ala Asn Phe Asn Asn Tyr
                260                 265                 270
Leu Asn Gln Ser Gly Ile Thr Lys Phe Asn Thr Ile Ile Gly Gly Lys
                275                 280                 285
Phe Val Asn Gly Glu Asn Thr Lys Arg Lys Gly Ile Asn Glu Tyr Ile
                290                 295                 300
Asn Leu Tyr Ser Gln Gln Ile Asn Asp Lys Thr Leu Lys Lys Tyr Lys
305                 310                 315                 320
Met Ser Val Leu Phe Lys Gln Ile Leu Ser Asp Thr Glu Ser Lys Ser
                325                 330                 335
Phe Val Ile Asp Lys Leu Glu Asp Asp Ser Asp Val Val Thr Thr Met
                340                 345                 350
Gln Ser Phe Tyr Glu Gln Ile Ala Ala Phe Lys Thr Val Glu Glu Lys
                355                 360                 365
Ser Ile Lys Glu Thr Leu Ser Leu Leu Phe Asp Asp Leu Lys Ala Gln
                370                 375                 380
Lys Leu Asp Leu Ser Lys Ile Tyr Phe Lys Asn Asp Lys Ser Leu Thr
385                 390                 395                 400
Asp Leu Ser Gln Gln Val Phe Asp Asp Tyr Ser Val Ile Gly Thr Ala
                405                 410                 415
Val Leu Glu Tyr Ile Thr Gln Gln Ile Ala Pro Lys Asn Leu Asp Asn
                420                 425                 430
Pro Ser Lys Lys Glu Gln Glu Leu Ile Ala Lys Lys Thr Glu Lys Ala
                435                 440                 445
Lys Tyr Leu Ser Leu Glu Thr Ile Lys Leu Ala Leu Glu Glu Phe Asn
                450                 455                 460
Lys His Arg Asp Ile Asp Lys Gln Cys Arg Phe Glu Glu Ile Leu Ala
465                 470                 475                 480
Asn Phe Ala Ala Ile Pro Met Ile Phe Asp Glu Ile Ala Gln Asn Lys
                485                 490                 495
Asp Asn Leu Ala Gln Ile Ser Ile Lys Tyr Gln Asn Gln Gly Lys Lys
                500                 505                 510
```

```
Asp Leu Leu Gln Ala Ser Ala Glu Asp Val Lys Ala Ile Lys Asp
            515                 520                 525

Leu Leu Asp Gln Thr Asn Asn Leu Leu His Lys Leu Lys Ile Phe His
        530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
    690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
        835                 840                 845

Ile Ala Asn Lys Asn Lys Asp Asn Pro Lys Lys Glu Ser Val Phe Glu
    850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
        915                 920                 925
```

```
Val Asp Gly Lys Gly Asn Ile Ile Lys Gln Asp Thr Phe Asn Ile Ile
930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
                980                 985                 990

Ala Lys Leu Val Ile Glu Tyr Asn Ala Ile Val Val Phe Glu Asp Leu
            995                 1000                1005

Asn Phe Gly Phe Lys Arg Gly Arg Phe Lys Val Glu Lys Gln Val
    1010                1015                1020

Tyr Gln Lys Leu Glu Lys Met Leu Ile Glu Lys Leu Asn Tyr Leu
    1025                1030                1035

Val Phe Lys Asp Asn Glu Phe Asp Lys Thr Gly Gly Val Leu Arg
    1040                1045                1050

Ala Tyr Gln Leu Thr Ala Pro Phe Glu Thr Phe Lys Lys Met Gly
    1055                1060                1065

Lys Gln Thr Gly Ile Ile Tyr Tyr Val Pro Ala Gly Phe Thr Ser
    1070                1075                1080

Lys Ile Cys Pro Val Thr Gly Phe Val Asn Gln Leu Tyr Pro Lys
    1085                1090                1095

Tyr Glu Ser Val Ser Lys Ser Gln Glu Phe Phe Ser Lys Phe Asp
    1100                1105                1110

Lys Ile Cys Tyr Asn Leu Asp Lys Gly Tyr Phe Glu Phe Ser Phe
    1115                1120                1125

Asp Tyr Lys Asn Phe Gly Asp Lys Ala Ala Lys Gly Lys Trp Thr
    1130                1135                1140

Ile Ala Ser Phe Gly Ser Arg Leu Ile Asn Phe Arg Asn Ser Asp
    1145                1150                1155

Lys Asn His Asn Trp Asp Thr Arg Glu Val Tyr Pro Thr Lys Glu
    1160                1165                1170

Leu Glu Lys Leu Leu Lys Asp Tyr Ser Ile Glu Tyr Gly His Gly
    1175                1180                1185

Glu Cys Ile Lys Ala Ala Ile Cys Gly Glu Ser Asp Lys Lys Phe
    1190                1195                1200

Phe Ala Lys Leu Thr Ser Val Leu Asn Thr Ile Leu Gln Met Arg
    1205                1210                1215

Asn Ser Lys Thr Gly Thr Glu Leu Asp Tyr Leu Ile Ser Pro Val
    1220                1225                1230

Ala Asp Val Asn Gly Asn Phe Phe Asp Ser Arg Gln Ala Pro Lys
    1235                1240                1245

Asn Met Pro Gln Asp Ala Asp Ala Asn Gly Ala Tyr His Ile Gly
    1250                1255                1260

Leu Lys Gly Leu Met Leu Leu Gly Arg Ile Lys Asn Asn Gln Glu
    1265                1270                1275

Gly Lys Lys Leu Asn Leu Val Ile Lys Asn Glu Glu Tyr Phe Glu
    1280                1285                1290

Phe Val Gln Asn Arg Asn Asn
    1295                1300

<210> SEQ ID NO 28
<211> LENGTH: 23
<212> TYPE: DNA
```

```
<213> ORGANISM: artificial sequence
<220> FEATURE:
<223> OTHER INFORMATION: Transcription Control and Labeling Cassette

<400> SEQUENCE: 28
cctttctcgt gaactagtca tgg                                              23
```